(12) United States Patent
Berriel Diaz et al.

(10) Patent No.: US 9,879,258 B2
(45) Date of Patent: Jan. 30, 2018

(54) TREATMENT OF INSULIN RESISTANCE THROUGH INHIBITORS OF TRANSCRIPTION FACTOR TSC22D4

(71) Applicants: Deutsches Krebsforschungszentrum Stiftung Des Oeffentlichen Rechts, Heidelberg (DE); Ruprecht-Karls-Universitaet Heidelberg, Heidelberg (DE)

(72) Inventors: Mauricio Berriel Diaz, Dossenheim (DE); Stephan Herzig, Vaterstetten (DE); Kilian Friedrich, Heidelberg (DE); Allan Jones, Heidelberg (DE)

(73) Assignees: DEUTSCHES KREBSFORSCHUNGSZENTRUM STIFTUNG DES OFFENTLICHEN RECHTS, Heidelberg (DE); RUPRECHT-KARLS-UNIVERSITAT HEIDELBERG, Heidelberg (DE)

( * ) Notice: Subject to any disclaimer, the term of this patent is extended or adjusted under 35 U.S.C. 154(b) by 0 days.

(21) Appl. No.: 14/787,416

(22) PCT Filed: Jun. 17, 2014

(86) PCT No.: PCT/EP2014/062713
§ 371 (c)(1),
(2) Date: Oct. 27, 2015

(87) PCT Pub. No.: WO2014/202602
PCT Pub. Date: Dec. 24, 2014

(65) Prior Publication Data
US 2016/0115475 A1    Apr. 28, 2016

(30) Foreign Application Priority Data

Jun. 17, 2013   (EP) .................. 13172362

(51) Int. Cl.
*C12N 15/11* (2006.01)
*C12N 15/113* (2010.01)
*G01N 33/50* (2006.01)
*G01N 33/68* (2006.01)
*C12Q 1/68* (2006.01)

(52) U.S. Cl.
CPC .......... *C12N 15/113* (2013.01); *C12Q 1/6883* (2013.01); *G01N 33/5008* (2013.01); *G01N 33/6872* (2013.01); *G01N 33/6893* (2013.01); *C12N 2310/14* (2013.01); *C12N 2310/141* (2013.01); *C12N 2310/531* (2013.01); *C12N 2320/30* (2013.01); *C12Q 2600/136* (2013.01); *C12Q 2600/158* (2013.01); *G01N 2333/4703* (2013.01); *G01N 2500/04* (2013.01); *G01N 2500/10* (2013.01); *G01N 2800/042* (2013.01)

(58) Field of Classification Search
CPC ............ C12N 15/1136; C12N 2310/11; C12N 2310/14
See application file for complete search history.

(56) References Cited

U.S. PATENT DOCUMENTS

2009/0215895 A1* 8/2009 Ferrante .................. C07C 57/03
514/560

FOREIGN PATENT DOCUMENTS

| WO | WO 2005/059564 A1 | 6/2005 |
| WO | WO2012/061754 A2 * | 5/2012 |
| WO | WO 2012/158123 A1 | 11/2012 |
| WO | WO 2013/076501 A2 | 5/2013 |

OTHER PUBLICATIONS

What's Wrong with Wikipedia? A Publication of the Harvard College Writing Program, http://isites.harvard.edu/icb/icb.do?keyword=k70847&pageid=icb.page346376, p. 1 retrieved on Nov. 22, 2016.*
Mayo Clinic, Metabolic syndrome Symptom and causes, http://www.mayoclinic.org/diseases-conditions/metabolic-syndrome/symptoms-causes/dxc-20197520?p=1, p. 1, retrieved on Nov. 22, 2016).*
Lam et al. Molecular Therapy-Nucleic Acids, 2015, e252, pp. 1-20.*
Tenebaum et al. Cardiovascular Diabetaology 2003, 2:4, pp. 1-7.*
Carré, Nadège et al., "Dual Effect of the Adapter Growth Factor Receptor-Bound Protein 14 (Grb14) on Insulin Action in Primary Hepatocytes", *Endocrinology*, 2008, 149(6):3109-3117.
Cho, Kae Won et al., "Lipocalin-13 Regulates Glucose Metabolism by both Insulin-Dependent and Insulin-Independent Mechanisms," *Molecular and Cellular Biology*, Feb. 2011, 31(3):450-457.
Jones, Allan et al., "TSC22D4 is a molecular output of hepatic wasting metabolism," *EMBO Molecular Medicine*, 2013, 5(2):294-308.
Liu, Tao et al., "Cistrome: an integrative platform for transcriptional regulation studies," *Genome Biology*, 2011, 12(8):1-10.
Taniguchi, Cullen M., et al., "Critical nodes in signaling pathways: insights into insulin action," *Nature Reviews: Molecular Cell Biology*, Feb. 2006, 7(2):85-96.

* cited by examiner

*Primary Examiner* — Brian Whiteman
(74) *Attorney, Agent, or Firm* — Saliwanchik, Lloyd & Eisenschenk

(57) ABSTRACT

The present invention relates to modulators, in particular inhibitors, of TSC22D4 activity or expression and their uses for the prevention, treatment, and/or regulation of insulin resistance, metabolic syndrome and/or diabetes and/or for improving insulin sensitivity in mammal. The present invention further relates to screening methods in order to identify these modulators, the use of modulators as identified in the diagnosis of these diseases, as well as kits, comprising materials for performing the methods according to the present invention.

2 Claims, 24 Drawing Sheets

Figure 1:
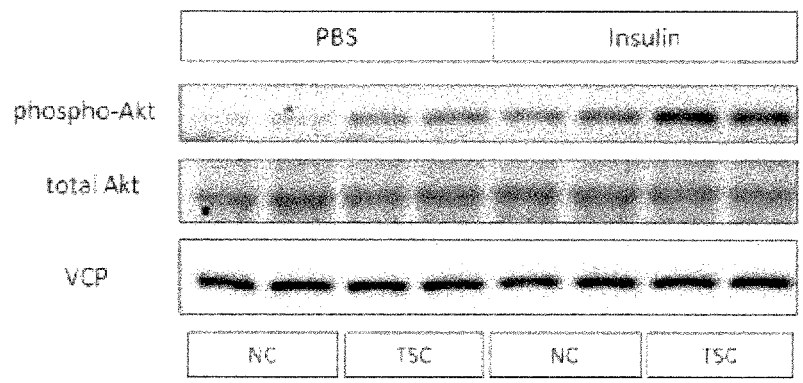

TREATMENT OF INSULIN RESISTANCE THROUGH INHIBITORS OF TRANSCRIPTION FACTOR TSC22D4

CROSS REFERENCE TO RELATED APPLICATIONS

This application is a National Stage Application of International Application Number PCT/EP2014/062713, filed Jun. 17, 2014; which claims priority to European Application No. 13172362.9, filed Jun. 17, 2013; both of which are incorporated herein by reference in their entirety.

The Sequence Listing for this application is labeled "SeqList-23Oct15.txt", which was created on Oct. 23, 2015, and is 2 KB. The entire content is incorporated herein by reference in its entirety.

The present invention relates to modulators, in particular inhibitors, of TSC22D4 activity or expression and their uses for the prevention, treatment, and/or regulation of insulin resistance, metabolic syndrome and/or diabetes and/or for improving insulin sensitivity in mammal. The present invention further relates to screening methods in order to identify these modulators, the use of modulators as identified in the diagnosis of these diseases, as well as kits, comprising materials for performing the methods according to the present invention.

BACKGROUND OF THE INVENTION

In humans, a combination of excessive lipid storage and decreased removal leads to overweight and associated co-morbidities, including insulin resistance, cardiovascular complications, and dyslipidemia (Langin D. In and out: adipose tissue lipid turnover in obesity and dyslipidemia. Cell Metab. 2011 Nov. 2; 14(5):569-70), now affecting more than 1.5 billion people worldwide (Finucane M M, et al. National, regional, and global trends in body-mass index since 1980: systematic analysis of health examination surveys and epidemiological studies with 960 country-years and 91 million participants. Lancet. 2011 Feb. 12; 377 (9765):557-67). Indeed, insulin resistance represents the core component of the so-called metabolic syndrome, ultimately leading to the development of metabolic dysfunction, such as glucose intolerance, pancreatic beta cell failure, and eventually type 2 diabetes.

Impaired insulin secretion (beta-cell), increased hepatic glucose production (liver), and decreased peripheral (muscle) glucose utilization constitute the traditional primary defects responsible for the development and progression of type 2 diabetes mellitus. beta-Cell failure, ultimately leading to decreased insulin secretion, is now known to occur much earlier in the natural history of type 2 diabetes than originally believed. Additionally, a better understanding of the pathophysiology of type 2 diabetes reveals other etiologic mechanisms beyond the classic triad, now referred to as the ominous octet. In addition to the beta-cell, liver, and muscle, other pathogenic mechanisms include adipocyte insulin resistance (increased lipolysis), reduced incretin secretion/sensitivity (gastrointestinal), increased glucagon secretion (alphacell), enhanced glucose reabsorption (kidney), and central nervous system insulin resistance resulting from neurotransmitter dysfunction (brain). Currently, the management of type 2 diabetes focuses on glucose control via lowering of blood glucose (fasting and postprandial) and hemoglobin A(1c). However, the goal of therapy should be to delay disease progression and eventual treatment failure. Treatment should target the known pathogenic disturbances of the disease (i.e., reducing the deterioration of beta-cell function and improving insulin sensitivity). In recent years, treatment strategies have focused on the development of novel therapeutic options that affect many of the defects contributing to type 2 diabetes and that provide durable glucose control through a blunting of disease progression. Optimal management of type 2 diabetes should include early initiation of therapy using multiple drugs, with different mechanisms of action, in combination (DeFronzo R A. Current issues in the treatment of type 2 diabetes. Overview of newer agents: where treatment is going. Am J Med. 2010 March; 123(3 Suppl):S38-48).

Especially the insensitivity of major metabolic organs against insulin action, including the liver, skeletal muscle and adipose tissue, substantially contributes to disease progression and the ultimate need for pharmacologic intervention to prevent diabetic late complications. Thus, efficient and safe insulin sensitization remains an attractive target and aim in anti-diabetic therapy.

Transcriptional co-factor complexes have been identified as important checkpoints in the coordination of metabolic programs in various tissues, including liver and white adipose tissue (WAT) (for a review, see Sommerfeld A, Krones-Herzig A, Herzig S. Transcriptional cofactors and hepatic energy metabolism. Mol Cell Endocrinol. 2011 Jan. 30; 332 (1-2): 21-31).

Kester H A, et al. (in: Transforming growth factor-beta-stimulated clone-22 is a member of a family of leucine zipper proteins that can homo- and heterodimerize and has transcriptional repressor activity. J Biol Chem. 1999 Sep. 24; 274(39):27439-47) describe that TGF-beta-stimulated clone-22 (TSC-22) encodes a leucine zipper-containing protein that is highly conserved during evolution.

Furthermore, Jones et al. (in Jones, A., et al., Transforming growth factor-beta1 Stimulated Clone-22 D4 is a molecular output of hepatic wasting metabolism. EMBO Mol Med. 2013 February; 5(2):294-308) describe that as a molecular cachexia output pathway, hepatic levels of the transcription factor transforming growth factor beta 1-stimulated clone (TSC) 22 D4 were increased in cancer cachexia. Mimicking high cachectic levels of TSC22D4 in healthy livers led to the inhibition of hepatic VLDL release and lipogenic genes, and diminished systemic VLDL levels under both normal and high fat dietary conditions. Therefore, hepatic TSC22D4 activity may represent a molecular rationale for peripheral energy deprivation in subjects with metabolic wasting diseases, including cancer cachexia.

Kulozik, Ph., et al. (Hepatic deficiency in transcriptional co-factor TBLI promotes liver steatosis and hypertriglyceridemia. 2011 Cell Metab. 13: 389-400) describe that the impaired hepatic expression of transcriptional cofactor transducin beta-like (TBL) 1 represents a common feature of mono- and multigenic fatty liver mouse models. The liver-specific ablation of TBL1 gene expression in healthy mice promoted hypertriglyceridemia and hepatic steatosis under both normal and high-fat dietary conditions. As TBL1 expression levels were found to also inversely correlate with liver fat content in human patients, the lack of hepatic TBL1/TBLR1 cofactor activity may represent a molecular rationale for hepatic steatosis in subjects with obesity and the metabolic syndrome.

Berriel Diaz, M., et al. (Nuclear receptor co-factor RIP140 controls lipid metabolism during wasting in mice. 2008. Hepatology 48: 782-791) describe that by preventing the mobilization of hepatic TG stores, the induction of RIP140 in liver provides a molecular rationale for hepatic steatosis in starvation, sepsis, or cancer cachexia. Inhibition of hepatic RIP140 transcriptional activity might, thereby, provide an attractive adjunct scheme in the treatment of these conditions.

Farese et al. (in: The problem of establishing relationships between hepatic steatosis and hepatic insulin resistance. Cell Metab. 2012 May 2; 15(5):570-3) describe that excessive deposition of fat in the liver (hepatic steatosis) is frequently accompanied by hepatic insulin resistance.

Major classes of anti-diabetic and/or insulin sensitizing drugs include sulfonyl ureas, metformin, thiazolidine diones, alpha-glucosidase inhibitors, incretin mimetics, and dipeptidylpeptidase 4 inhibitors, all of which are associated with severe limitations (for review see Moller, Metabolic disease drug discovery-"hitting the target" is easier said than done. Cell Metab. 2012 Jan. 4; 15(1):19-24).

Despite the key role of insulin resistance in the pathogenesis of type 2 diabetes, effective and safe insulin sensitizers are still lacking. Indeed, current drugs of the thiazolidinedione family display a moderate efficacy profile and are accompanied by substantial side effects, including weight gain, increased risk of heart failure, possible increased risk of bladder cancer, and an increased risk for myocardial infarction, e.g. leading to the recent market withdrawal of rosiglitazone.

It is therefore an object of the present invention to provide novel targets and strategies to prevent, treat, and/or regulate insulin resistance, metabolic syndrome and/or diabetes and/or to improve insulin sensitivity According to a first aspect of the invention, the above object is solved by a method for identifying a modulator for the prevention, treatment, and/or regulation of insulin resistance, metabolic syndrome and/or diabetes type 1 or 2, and/or for improving insulin sensitivity, such as, for example, insulin sensitivity in the context of a tumorous disease in a mammal, comprising the steps of: a) providing a biological sample, comprising a nucleic acid sequence encoding for TSC22D4 or the gene expression product of TSC22D4, b) contacting said sample with at least one putative modulator of said nucleic acid sequence encoding for TSC22D4 or the gene expression product of TSC22D4, and c) detecting a binding between said at least one putative modulator and said nucleic acid sequence encoding for TSC22D4 or the gene expression product of TSC22D4, and d) identifying said modulator of said nucleic acid sequence encoding for TSC22D4 or the gene expression product of TSC22D4.

The present inventors have shown that the transcriptional regulator transforming growth factor beta 1 stimulated clone 22 D4 (TSC22D4) controls hepatic and systemic insulin sensitivity. Thus, TSC22D4 represents a defined molecular and organ-specific target, regulating several key nodes in the insulin signalling cascade, thereby enhancing hepatic and systemic insulin sensitivity and normalizing diabetic hyperglycaemia. The transcriptional TSC22D4 complex serves as a novel molecular target for interference-based strategies that can be manipulated in order to improve insulin sensitivity and restore normal glucose homeostasis in diabetic conditions. Furthermore, in the experiments that were performed in the context of the present invention, a liver-specific loss of TSC22D4 significantly improved glucose tolerance and insulin sensitivity, and counter-acted hyperinsulinemia. The TSC22D4 complex was identified as a novel molecular checkpoint in hepatic and systemic insulin sensitization and knock-down strategies (mediated by shRNA, siRNA and miRNA technologies) have been developed. The manipulation of TSC22D4 in liver with liver-specific targeting approaches (e.g. siRNA-based knockdown strategies) should avoid major side effects in other tissues.

In more detail, ChIP-sequence analysis of the TSC22D4 (NM 030935) cistrome in combination with high throughput TSC22D4 target transcriptome studies in healthy animals revealed that major nodes of the insulin signalling pathway were directly or indirectly targeted by TSC22D4, most notably lipocalin 13, Grb14, and SOCS 2/3. Down-regulation or overexpression of TSC22D4 in primary mouse hepatocytes as well as in wild-type mice led to the up- or down-regulation of the intracellular insulin signalling pathway, respectively, as determined by phosphorylation of Akt/PKB kinase at Ser473 and of GSK3beta at Ser9, in response to acute insulin exposure, respectively.

Hepatic inactivation of TSC22D4 in diabetic db/db mice improved glucose intolerance and insulin resistance in these animals and normalized blood glucose to almost healthy levels. In congruence with an overall improvement of the metabolic status in diabetic animals, circulating levels of pro-inflammatory cytokines and resistin were significantly lower in mice with liver-specific TSC22D4 deficiency. Of note, inactivation of TSC22D4 in hepatoma cells did not increase cellular growth but rather decreased proliferation, suggesting that the insulin sensitizing function of TSC22D4 does not result in increased cancer susceptibility in affected cells/organs.

Preferred is a method according to the present invention which further comprises the step of assessing the TSC22D4 activity and/or expression in the presence or absence of said modulator, wherein a decrease between the measured activity or expression of TSC22D4 in the presence of said modulator compared to the measured activity or expression of TSC22D4 in the absence of said modulator indicates that said modulator is for use in the prevention, treatment, and/or regulation of insulin resistance, metabolic syndrome and/or diabetes type 1 or 2, and/or for improving insulin sensitivity, such as, for example, insulin sensitivity in the context of a tumorous disease in a mammal, comprising the steps of More preferably, said activity or expression of TSC22D4 is hepatic activity or expression, that is, activity and/or expression in liver cells or tissue.

More preferred is a method according to the present invention, wherein said activity or expression of TSC22D4 is hepatic activity or expression. Thus, the activity and/or expression is tested in liver cells or tissue.

In one embodiment, the biological sample of the method according to the present invention is contacted with the candidate compound in vitro or in vivo.

In yet another aspect of the method according to the present invention, said method further comprises the step of analyzing the effect of said modulator in the prevention, treatment, and/or regulation of insulin resistance, metabolic syndrome and/or diabetes type 1 or 2, and/or for improving insulin sensitivity, such as, for example, insulin sensitivity in the context of a tumorous disease. Preferred is a method according to present invention, further comprising the step of analyzing blood glucose, circulating levels of pro-inflammatory cytokines, and or resistin in a biological sample derived from said mammal. Such testing thus may involve the analysis of markers in a biological sample take from the subject to be tested, such as, for example, insulin concentration, c-peptide concentration, interleukin-6 concentration, leptin concentration, resistin concentration, TNF alpha concentration, glucagon concentration and/or PYY concentration, preferably in the presence or absence of the said modulator. Respective assays are known to the person of skill.

Preferred is a method according to present invention, wherein said modulator is a candidate compound selected from a peptide library molecule, an aptamer, a combinatory library molecule, a cell extract derived molecule, a small molecular drug, a bacterial metabolite, a phage display molecule, an antibody or fragment thereof, a protein, a protein fragment, a polynucleotide, an oligonucleotide, in particular a miRNA, siRNA or shRNA, and combinations thereof, which preferably targets and modulates expression of TSC22D4, and thus can also alter the corresponding activity of the gene product. For clarity, "targeting" includes binding directly or indirectly to a gene product, or functional site, of such a product (e.g., antibody binding and neutralizing TSC22D4, thus modulating its activity).

In one aspect, the bioactive agent utilizes "RNA interference (RNAi)". RNAi is a process of sequence-specific, post-transcriptional gene silencing initiated by double stranded RNA (dsRNA) or siRNA. RNAi is seen in a number of organisms such as *Drosophila*, nematodes, fungi and plants, and is believed to be involved in anti-viral defense, modulation of transposon activity, and regulation of gene expression. During RNAi, dsRNA or siRNA induces degradation of target mRNA with consequent sequence-specific inhibition of gene expression. As used herein, a "small interfering RNA" (siRNA) is a RNA duplex of nucleotides that is targeted to the gene of TSC22D4. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' and/or 5' overhang portions. In some embodiments, the overhang is a 3' and/or a 5' overhang 0, 1, 2, 3, 4 or 5 nucleotides in length. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

In yet a further embodiment of the method as described above, assessing the activity of TSC22D4 comprises an enzyme activity assay, immunoassay, or Western blotting, preferably at least one method for the functional analysis of a transcription factor, such as, for example, reporter assays. In one embodiment, assessing the expression of TSC22D4 comprises Northern blotting, microarray analysis, RNA hybridization, methylation analysis, and/or RT-PCR. Assessing the activity of an enzyme or assessing the expression of a gene comprises all methods for assessing the activity of an enzyme (here transcription factor) known to the skilled person.

Accordingly, as an alternative, enzyme or expression activity of TSC22D4 can be assessed indirectly by assessing enzyme or expression activity of enzymes that are regulated by TSC22D4. Such testing thus may involve the analysis of markers in a biological sample take from the subject to be tested, such as, for example, insulin concentration, c-peptide concentration, interleukin-6 concentration, leptin concentration, resistin concentration, TNF alpha concentration, glucagon concentration and/or PYY concentration, preferably in the presence or absence of the said modulator. Respective assays are known to the person of skill. Further methods according to the invention are microarray assays, as well as any method suitable for the detection of gene expression, or enzyme activity, known to the skilled person.

Another aspect of the present invention then relates to a modulator that is specific for TSC22D4, and which is identified according to a method according to the present invention as described herein, wherein said modulator is selected from the group of a peptide library molecule, an aptamer, a combinatory library molecule, a cell extract derived molecule, a small molecular drug, a bacterial metabolite, a phage display molecule, an antibody or fragment thereof, a protein, a protein fragment, a polynucleotide, an oligonucleotide, in particular an miRNA, siRNA or shRNA, and combinations thereof. Preferably, said modulator is selected from an inhibitor of the expression and/or biological activity of TSC22D4.

In one embodiment, the inhibitor of TSC22D4 is selected from antisense DNA- and/or RNA-oligonucleotides, antisense 2'-O-methyl oligoribonucleotides, antisense oligonucleotides containing phosphorothioate linkages, small-interfering RNA, miRNA, antisense oligonucleotides containing Locked Nucleic Acid LNA® bases, morpholino antisense oligos, PPAR-gamma agonists, antagomirs, and mixtures thereof, and in particular an antagomir of TSC22D4.

In yet another aspect of the present invention, the modulator can be part of a fusion protein, is part of a carrier molecule that optionally comprises at least one anti-diabetic agent, such as, for example, a chemotherapeutic, peptide, small molecule drug, and/or radionucleotide that is conjugated to said modulator, and/or is part of a diagnostic agent that optionally comprises at least one detectable moiety. This is of particular advantage in the diagnostic context of the present invention, and/or for a more efficient, preferably synergistic, treatment together with other anti-diabetic agents.

The object of the is also solved by a method for producing a pharmaceutical composition, comprising the steps of: a) optionally, performing a method according to the present invention as above, and b) formulating said at least one modulator as identified or a modulator according to the present invention, with at least one pharmaceutically acceptable excipient. The carrier and/or excipient of the pharmaceutical composition must be "acceptable" in the sense of being compatible with the other ingredients of the formulation and not deleterious to the recipient thereof.

The object is further solved by a pharmaceutical composition, produced according to the present invention. In yet another embodiment, the pharmaceutical composition according to the present invention is for administration and/or is administered orally, rectally, transmucosally, transdermally, intestinally, parenterally, intramuscularly, intrathecally, direct intraventricularly, intravenously, intraperitoneally, intranasally, intraocularly, or subcutaneously.

The object is further solved by a modulator according to the present invention or the pharmaceutical composition according to the present invention for use in the diagnosis of diseases and/or for use in the prevention, regulation, and/or treatment of diseases. Preferred is a modulator or the pharmaceutical composition for use according to the present invention, wherein said disease is selected from insulin resistance, metabolic syndrome and/or diabetes. More preferably, the modulator or the pharmaceutical composition for use according to the present invention is selected from the group of a peptide library molecule, an aptamer, a combinatory library molecule, a cell extract derived molecule, a small molecular drug, a bacterial metabolite, a phage display molecule, an antibody or fragment thereof, a protein, a protein fragment, a polynucleotide, an oligonucleotide, in particular an miRNA, siRNA or shRNA, and combinations thereof. In one embodiment, the inhibitor of TSC22D4 is selected from antisense DNA- and/or RNA-oligonucleotides, antisense 2'-O-methyl oligoribonucleotides, antisense oligonucleotides containing phosphorothioate linkages, small-interfering RNA, miRNA, antisense oligonucleotides containing Locked Nucleic Acid LNA® bases, morpholino antisense oligos, PPAR-gamma agonists, antagomirs, and mixtures thereof, and in particular an antagomir of TSC22D4.

The object is further solved by a method for detecting and optionally diagnosing the presence or risk for a disease selected from insulin resistance, metabolic syndrome and/or diabetes type 1 or 2, and/or for improving insulin sensitivity, such as, for example, insulin sensitivity in the context of a tumorous disease, comprising the step of measuring the expression and/or biological activity of TSC22D4 in a biological sample obtained from a subject suspected to have such disease; wherein a decrease of the measured activity or expression of TSC22D4 in said sample compared to the measured activity or expression of TSC22D4 in a sample from a healthy subject indicates the presence or risk for a disease selected from insulin resistance, metabolic syndrome and/or diabetes type 1 or 2, and/or for improving insulin sensitivity, such as, for example, insulin sensitivity in the context of a tumorous disease. Preferably, said detecting comprises detecting binding of a modulator according to the present invention. Preferred is a method according to the present invention, wherein said sample is a biological sample, preferably selected from a blood, plasma, urine, cellular, and a tissue sample, such as, for example, a biopsy comprising liver, breast, prostate, bone, cartilage, lung, or brain tissue. A "biological sample" is a specimen of any biological source. The biological source can be any naturally occurring or genetically modified organism. The biological sample can derive from, without being limited to it, tissues, cell cultures, crude extracts, body fluids, as well as from solutions of gene expression products, nucleotide acids, proteins, or peptides, or nucleotide acids, proteins, or peptides as solid matter.

The object is further solved by a method for treating and/or preventing a disease selected from insulin resistance, metabolic syndrome and/or diabetes in a subject in need thereof, comprising the step of administering an effective amount of a modulator according to the present invention or the pharmaceutical composition according to the present invention to said patient in need thereof. Preferably, said modulator is selected from the group of a peptide library molecule, an aptamer, a combinatory library molecule, a cell extract derived molecule, a small molecular drug, a bacterial metabolite, a phage display molecule, an antibody or fragment thereof, a protein, a protein fragment, a polynucleotide, an oligonucleotide, in particular an miRNA, siRNA or shRNA, and combinations thereof. In one embodiment, the inhibitor of TSC22D4 is selected from antisense DNA- and/or RNA-oligonucleotides, antisense 2'-O-methyl oligoribonucleotides, antisense oligonucleotides containing phosphorothioate linkages, small-interfering RNA, siRNA, miRNA, antisense oligonucleotides containing Locked Nucleic Acid LNA® bases, morpholino antisense oligos, PPAR-gamma agonists, antagomirs, and mixtures thereof, and in particular an antagomir of TSC22D4.

The object is further solved by a diagnostic or therapeutic kit, comprising materials for performing a method according to the present invention, such as suitable enzymes and buffers for the diagnosis, optionally together with instructions for use of said kit. A kit for detecting TSC22D4 polypeptide preferably contains an antibody and/or miRNA that specifically binds TSC22D4 polypeptide. A kit for detecting TSC22D4 mRNA preferably contains one or more nucleic acids (e.g., one or more oligonucleotide primers or probes, DNA probes, RNA probes, or templates for generating RNA probes) that specifically hybridize with TSC22D4 mRNA.

Essentially the same holds true for therapeutic kits, which preferably contain pharmaceutically acceptable modulators for the TSC22D4 polypeptide and/or mRNA.

A "modulator" of TSC22D4 function and/or expression is a substance that regulates or changes the function and/or expression of TSC22D4. Such modulator may directly or indirectly influence TSC22D4 function and/or expression. TSC22D4 function and/or expression can be changed or regulated by, for example, and without being limited to it, binding to a domain of the TSC22D4 protein, or enhancing or suppressing gene expression of TSC22D4. A modulator according to the invention may also indirectly regulate or change the function and/or expression of TSC22D4 by regulating or changing the function and/or expression of a gene that regulates, or is regulated, by TSC22D4.

"Gene expression products" according to the invention comprise, but are not limited to, purified, recombinant, natural, artificial or synthetic nucleotide sequences, like DNA, cDNA, RNA, or mRNA; or proteins, or peptides. "Gene expression products" according to the invention comprise, but are not limited to, purified, recombinant, natural, artificial or synthetic gene expression products, or modifications thereof. A nucleic acid sequence according to the invention is any nucleic acid sequence encoding for TSC22D4 known in prior art, or complementary sequences, or nucleotide sequences hybridizing thereto under stringent conditions, as well as modifications thereof.

An "inhibitor" is a substance that can reduce the effectiveness of a catalyst in a catalysed reaction (either a non-biological catalyst or an enzyme). An inhibitor referred to herein can reduce the effectiveness of the activity of an enzyme; also, an inhibitor referred to herein can reduce the effectiveness of the expression of an enzyme. An inhibitor may be, without being limited to it, recombinant, natural, artificial or synthetic nucleotide sequences, like DNA, cDNA, RNA, miRNA or mRNA; or proteins (such as, for example, antibodies), or peptides, or modifications thereof. An inhibitor may be, without being limited to it, any nucleic acid sequence, or complementary sequences, or nucleotide sequences hybridizing under stringent conditions to a nucleotide sequence encoding for TSC22D4 known in prior art, as well as modifications thereof.

A "cell" according to the invention can be a prokaryotic or eukaryotic cell. A "cell" according to the invention is preferably, and without being limited to it, selected from liver cells. Mammalian cells may be preferably selected from a human, rabbit, mouse or rat. Preferably, the cell is a human cell. The term "cell" also includes cells of an animal model. Also, a cell can be part of a tissue culture.

The term "prevention" in the context of the present invention shall be understood as a medical intervention which aims to avoid the occurrence of a negative event which most likely leads to the worsening of the condition of a patient having a disease, or to the injury or the death of a healthy and/or ill subject.

A "subject in need thereof" can be, without being limited to it, any animal or human suffering of pain, especially neuropathic pain. Preferably, the subject in need thereof is a human.

Hepatocyte-specific inactivation of TSC22D4 enhanced insulin signaling in liver and skeletal muscle, while hepatic TSC22D4 overexpression blunted insulin tissue responses. Consequently, hepatic TSC22D4 inhibition both prevented and reversed hyperglycemia, glucose intolerance, and insulin resistance in various diabetes mouse models, respectively. TSC22D4 was found to exert its effects on systemic glucose homeostasis—in part—through the transcriptional regulation of the small secretory protein lipocalin (LCN) 13 as demonstrated by chromatin recruitment and genetic rescue experiments in vivo. As hepatic TSC22D4 levels were found to be elevated in human diabetic patients, correlating with decreased insulin sensitivity and hyperglycemia, the present invention establishes the inhibition of TSC22D4 as an attractive insulin sensitizing option in diabetes type 1 or 2 therapy as well as in the therapy of insulin resistance, metabolic syndrome and/or for improving insulin sensitivity, such as, for example, insulin sensitivity in the context of a tumorous disease.

The following figures, sequences, and examples merely serve to illustrate the invention and should not be construed to restrict the scope of the invention to the particular embodiments of the invention described in the examples. For the purposes of the present invention, all references as cited in the text are hereby incorporated in their entireties.

FIG. 1 shows that the knockdown of TSC22D4 in primary mouse hepatocytes enhances insulin signaling. Western blot of primary (1°) mouse hepatocytes treated with control or TSC22D4 shRNA adenovirus using total-Akt and Phospho-Akt (Ser473) antibodies (Cell signaling). Primary mouse hepatocytes were either incubated with PBS or Insulin for 10 minutes. shRNA-mediated knockdown of TSC22D4 resulted in an increase of Akt-phosphorylation.

Figure 2:
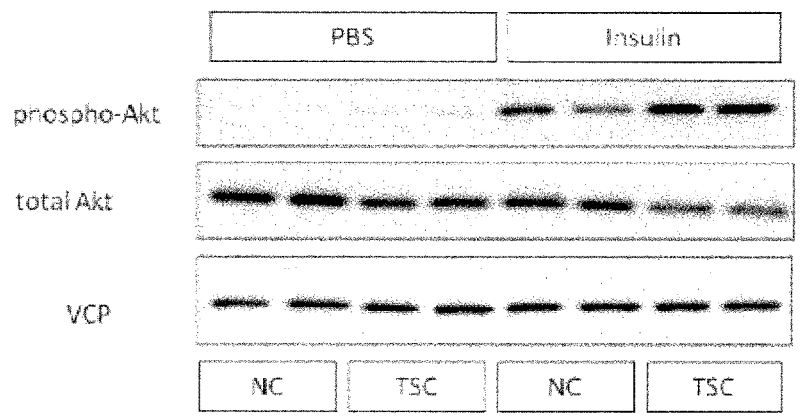
Figure 3A:
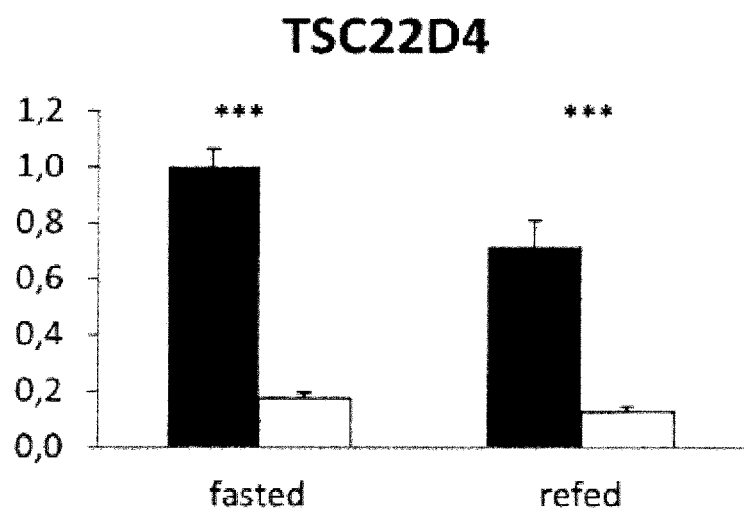
Figure 3B:
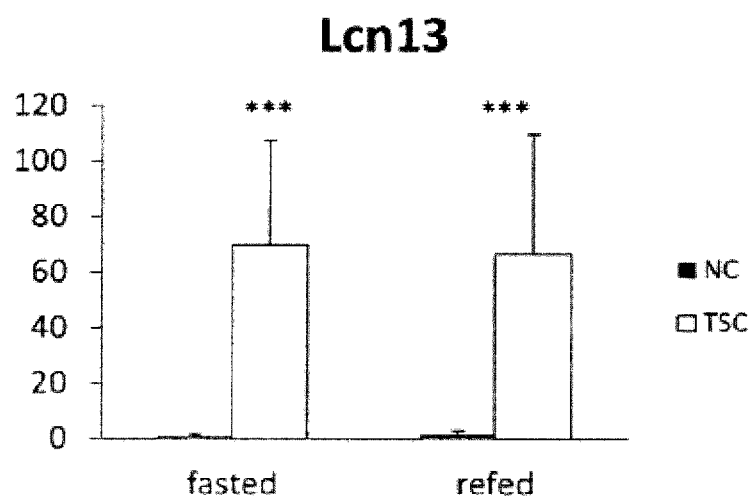
Figure 3C:
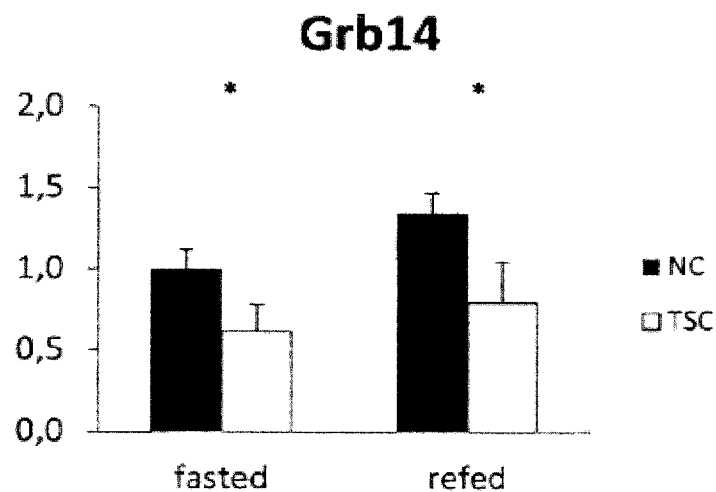
Figure 3D:
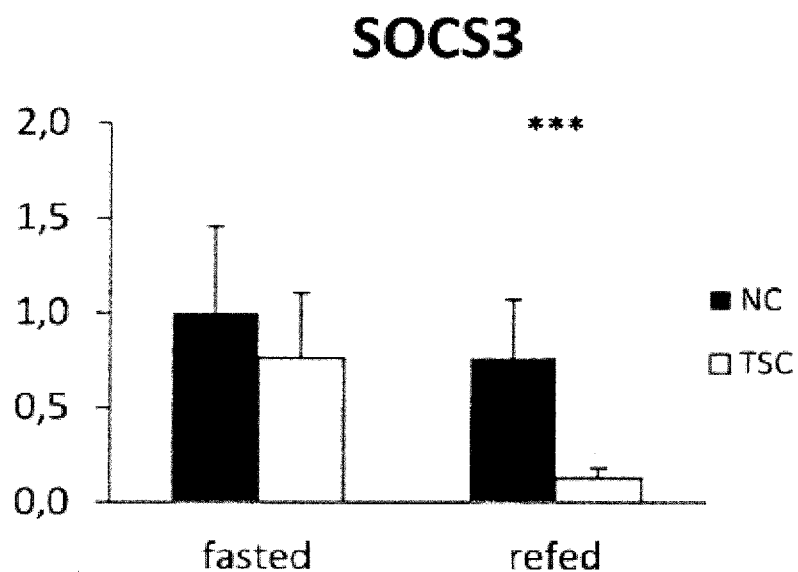
Figure 3E:
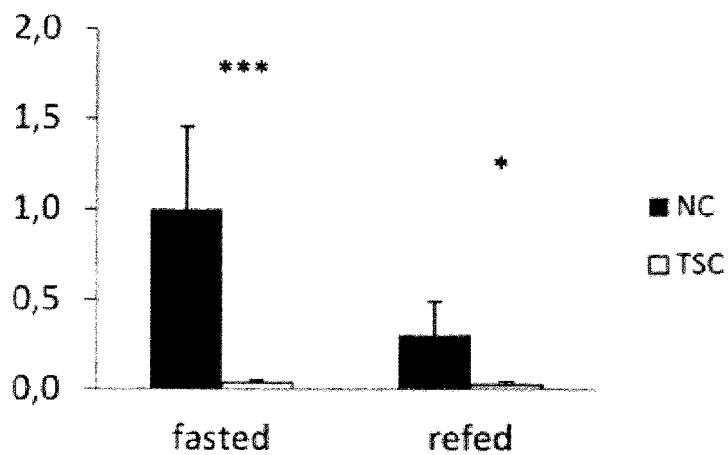

FIG. 2 shows that knockdown of hepatic TSC22D4 enhances insulin signaling in wild-type mice. Western blot of liver extracts from control or TSC22D4 shRNA adenovirus injected female C57Bl/6 mice 7 days after injection using total-Akt and Phospho-Akt (Ser473) antibodies (Cell signaling). 20 minutes prior to organ harvest, mice were injected intraperitoneally with either PBS or Insulin. Mice were fasted for 4 hours prior to the injection. shRNA-mediated knockdown of TSC22D4 resulted in an increase of Akt-phosphorylation after insulin stimulation.

FIGS. 3A-3E show that loss of hepatic TSC22D4 controls distinct components of the insulin signaling pathway in wild-type mice. Quantitative PCR analysis of FIG. 3A) transcription factor transforming growth factor beta 1-stimulated clone 22D4 (TSC22D4), FIG. 3B) Lipocalin 13 (Lcn13), FIG. 3C) Growth factor receptor-bound protein 14 (Grb14), FIG. 3D) suppressor of cytokine signaling 3 (SOCS3), FIG. 3E) adenylate cyclase 1 (ADCY1) in livers of control or TSC22D4 shRNA adenovirus-injected wild-type female C57Bl/6 mice in the fasted and refed state as in FIGS. 4A-4D (means±SEM, n=7). Statistical test FIGS. 3A-3E: Student's t-test.

Figure 4A:
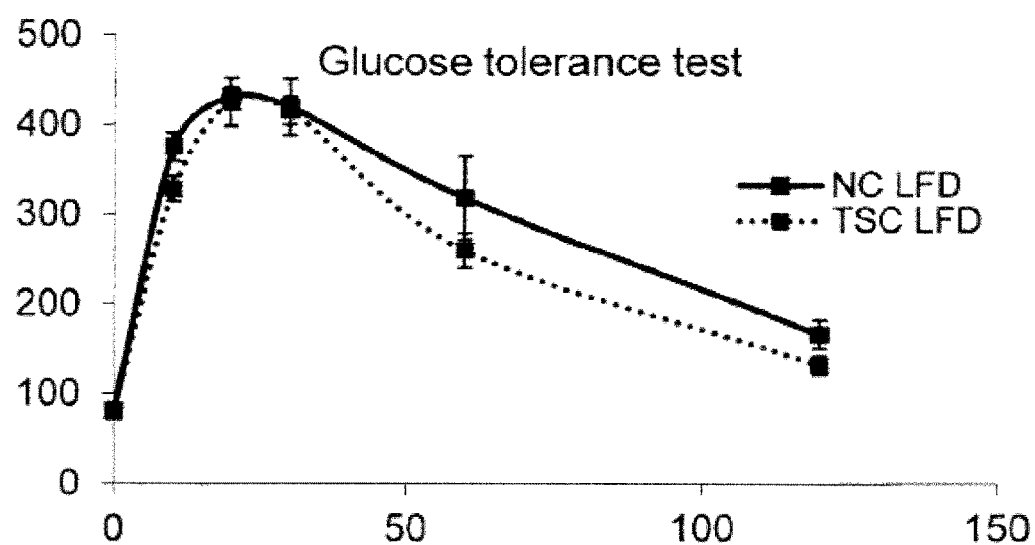
Figure 4B:
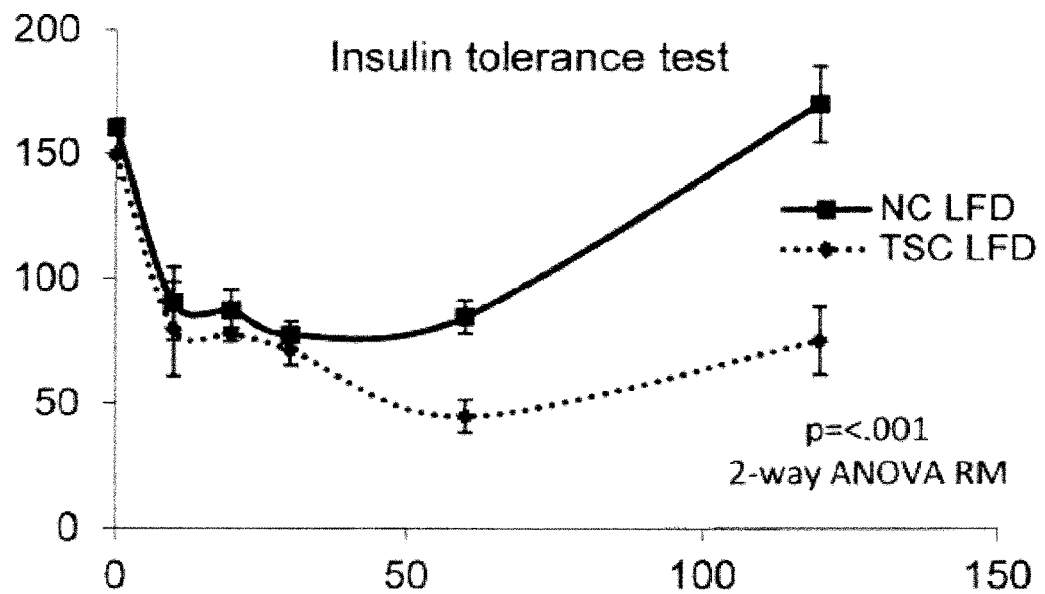
Figure 4C:
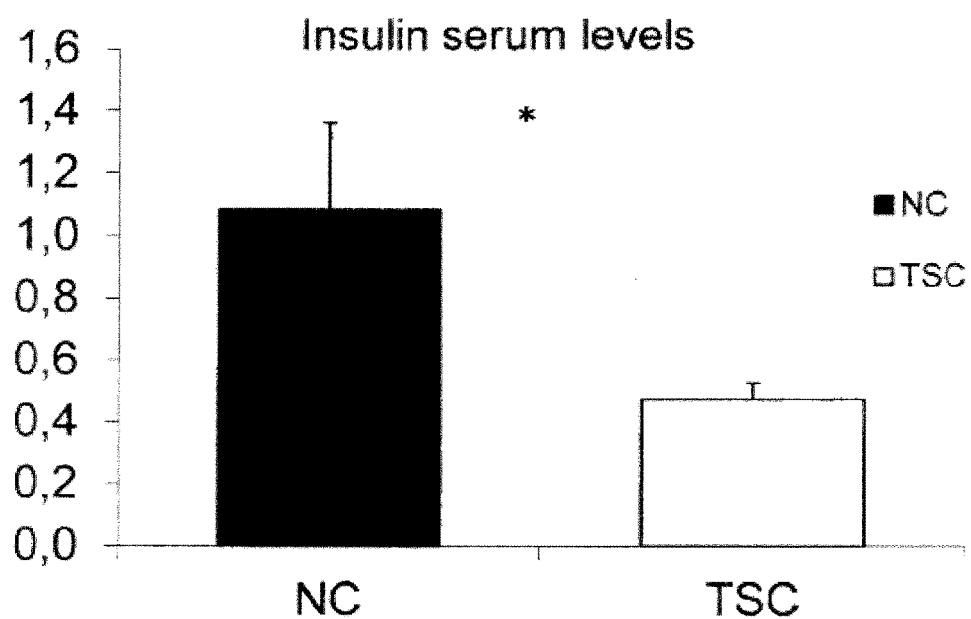
Figure 4D:
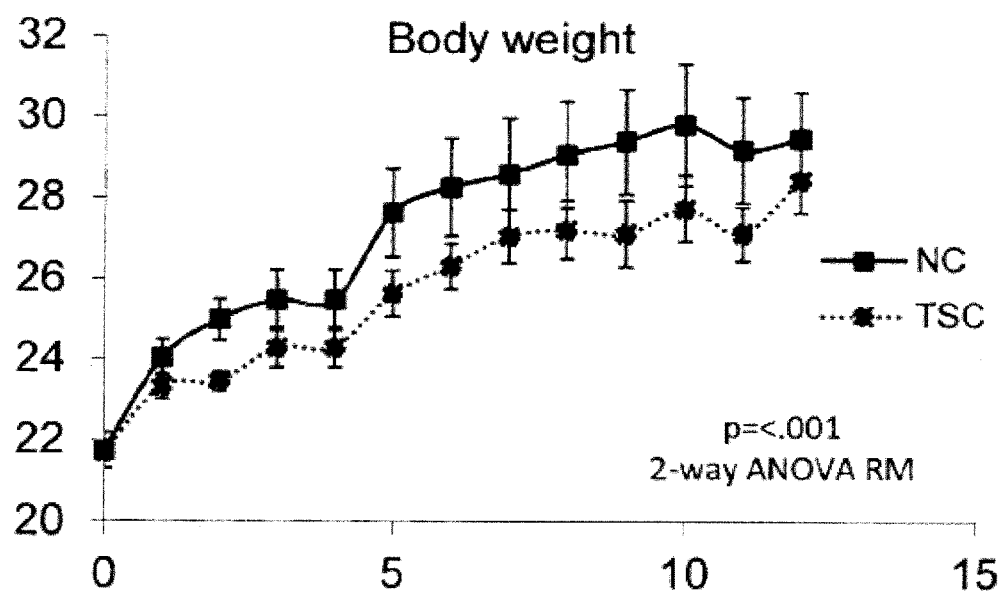

FIGS. 4A-4D show that the hepatocyte-specific inactivation of TSC22D4 improves glucose tolerance, insulin sensitivity and lowers insulin levels in wild-type animals. Low fat diet-fed C57Bl6 mice were injected with control or TSC22D4 miRNA adeno-associated virus for long-term and hepatocytes-specific knock-down of TSC 22D4. FIG. 4A) Eight weeks after virus injection mice were fasted for four hours before performing an Glucose tolerance test by intraperitoneally injecting 1 g Glucose per kg body weight. FIG. 4B) 9 weeks after virus injection mice were fasted for four hours before performing an Insulin tolerance test by intraperitoneally injecting 1 U Insulin per kg body weight. Knockdown of TSC22D4 resulted in a pronounced drop of blood sugar levels following i.p. insulin injection compared to control animals ($p<0.001$ TWO-WAY ANOVA RM; Holm-Sidak post hoc) indicating improved insulin sensitivity. Statistical test FIGS. 4A-4B, 4D: TWO-WAY ANOVA RM; Holm-Sidak post hoc. Statistical test FIG. 4C: Student's t-test.

Figure 5:
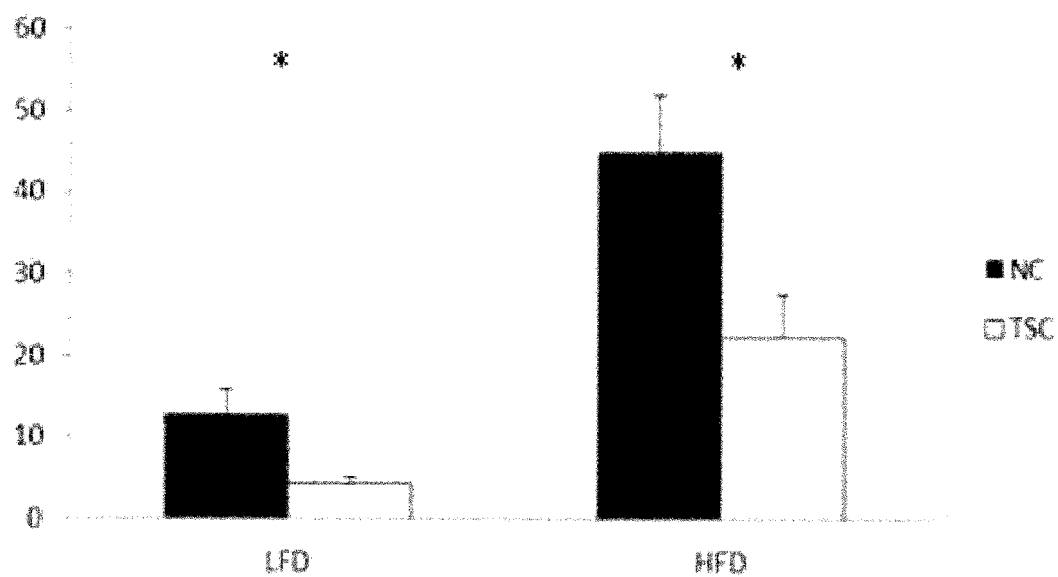

FIG. 5 shows that the insulin sensitivity is improved in long-term TSC22D4 knockdown under both low and high fat dietary conditions. Insulin resistance index (HOMA) in same animals as in FIGS. 6A-6D and in a corresponding high fat diet-fed cohort. (means±SEM, n=7)

Figure 6A:
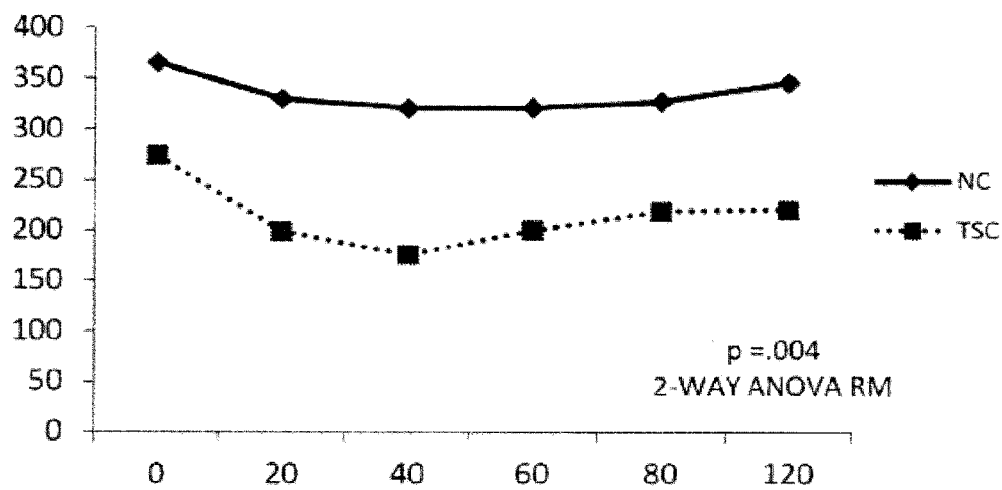
Figure 6B:
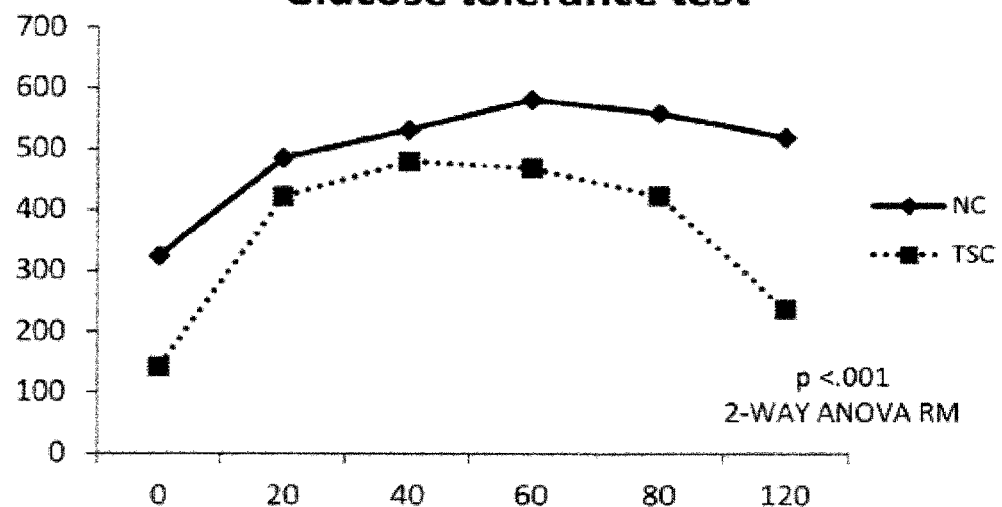
Figure 6C:
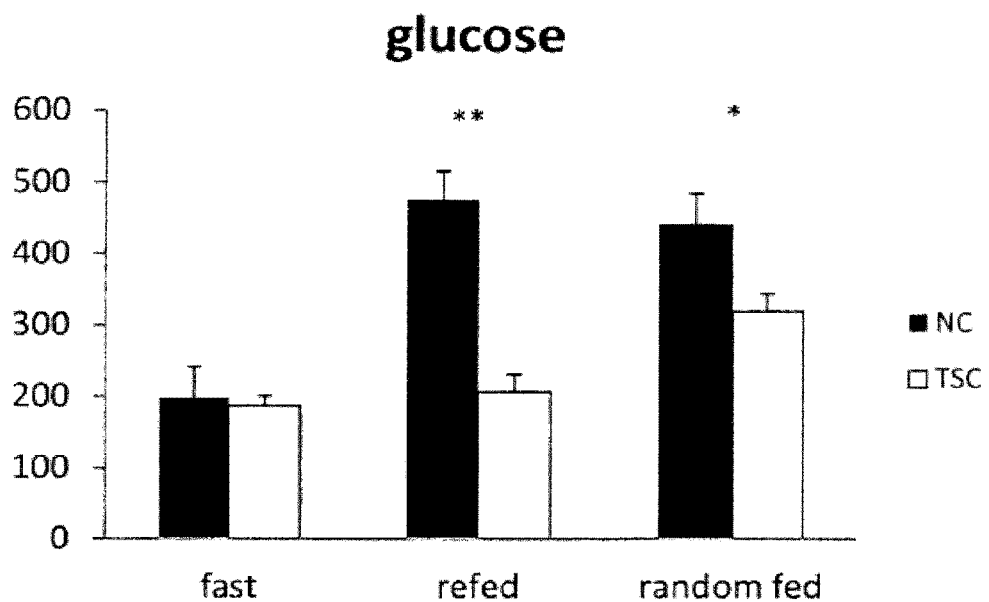
Figure 6D:
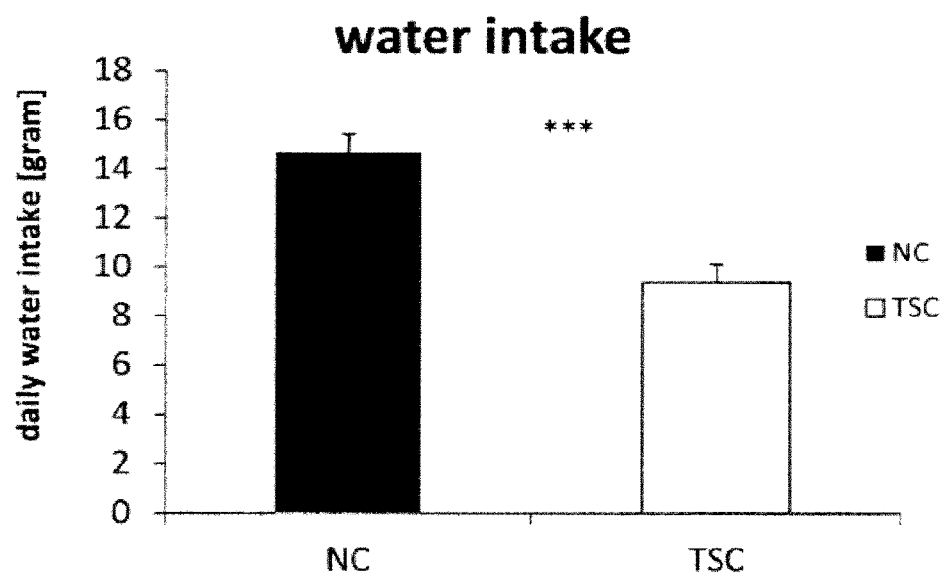

FIGS. 6A-6D show that the hepatic knockdown of TSC22D4 improves insulin sensitivity and normalizes in genetically diabetic mice. 11 week old db/db mice (a genetic mouse model for obesity) were injected with control or TSC22D4 shRNA adenovirus. FIG. 6A) 7 days after virus injection mice were fasted for four hours before performing an insulin tolerance test by intraperitoneally injecting 2 U Insulin per kg body weight. Knockdown of TSC22D4 resulted in a pronounced drop of blood sugar levels following i.p. insulin injection compared to control animals ($p=0.004$ TWO-WAY ANOVA RM; Holm-Sidak post hoc) indicating improved insulin sensitivity. FIG. 6B) 13 days after virus injection mice were fasted for four hours before performing a Glucose tolerance test by intraperitoneally injecting 1 g Glucose per kg body weight. Knockdown of TSC22D4 resulted in an improved metabolic response to i.p. Glucose injection compared to control animals ($p<0.001$; TWO-WAY ANOVA RM; Holm-Sidak post hoc) indicating improved insulin sensitivity. FIG. 6C) Mice were sacrificed in a fasted (for 18 hours), refed (fasted for 18 hours following 6 hours refeeding), or random fed state. Blood glucose levels (mg/dl) under fasting, refeeding, or random fed conditions (means±SEM, n=4). FIG. 6D) Daily water intake (gram) of db/db mice (means±SEM, n=12). Statistical test FIGS. 6A-6B: TWO-WAY ANOVA RM; Holm-Sidak post hoc. Statistical test FIGS. 6C-6D: Student's t-test.

Figure 7A:
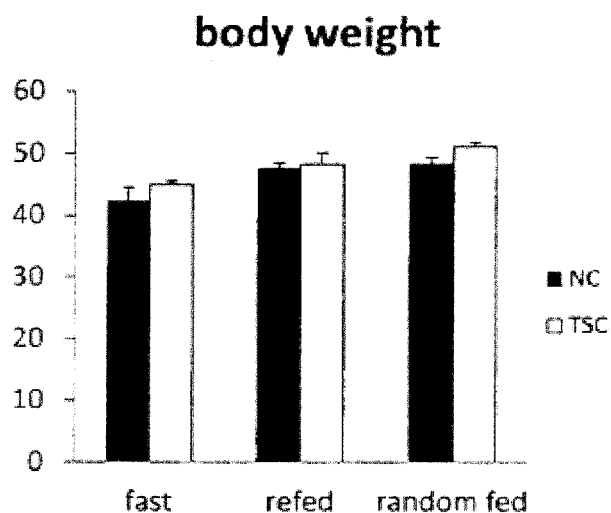
Figure 7B:
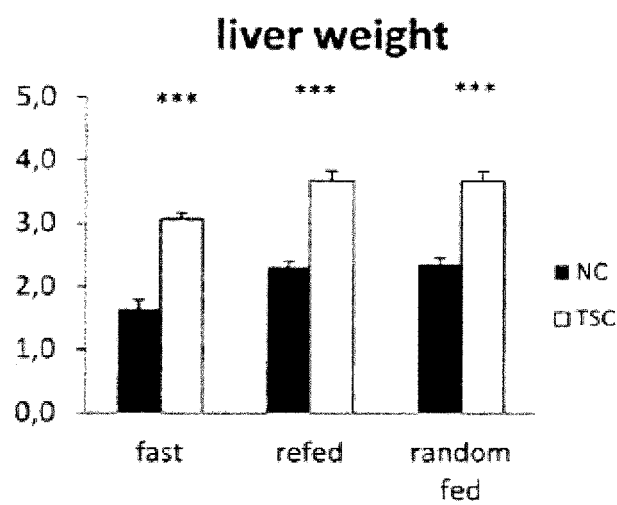
Figure 7C:
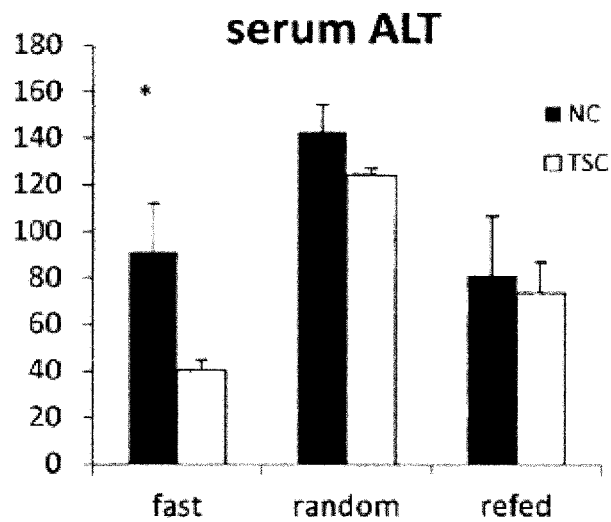
Figure 7D:
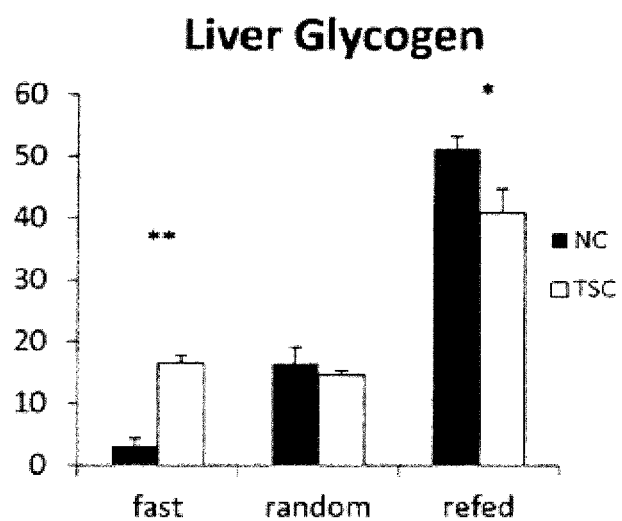
Figure 7E:
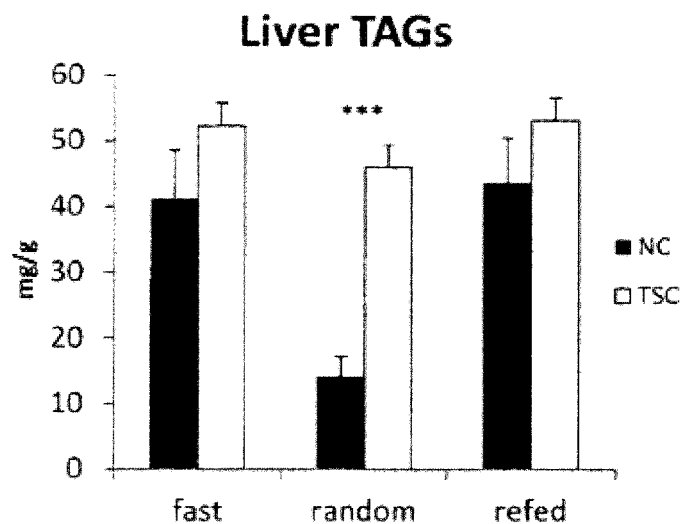
Figure 7F:
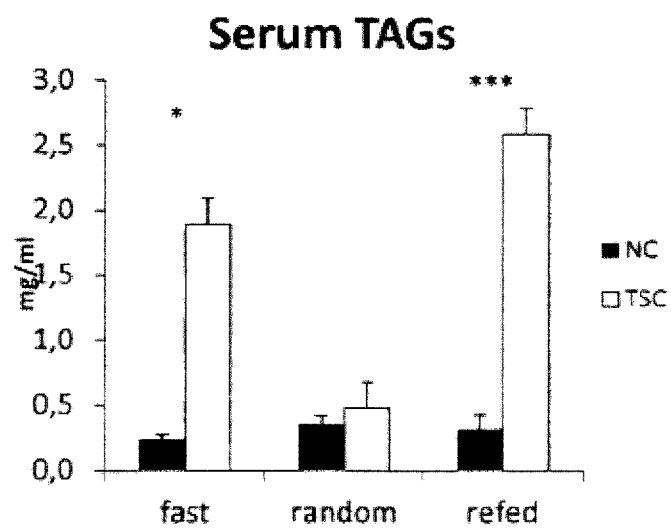

FIGS. 7A-7F shows body composition markers in db/db mice upon TSC22D4 knockdown. 11 week old db/db mice (same animals as in FIGS. 8A-8F) were injected with control or TSC22D4 shRNA adenovirus. Mice were sacrificed in a fasted (for 18 hours), refed (fasted for 18 hours following 6 hours refeeding), or random fed state. FIG. 7A) body weight in gram (means±SEM, n=4). FIG. 7B) liver weight in gram (means±SEM, n=4). FIG. 7C) Serum Alanin-Aminotransferase levels (ALT; means±SEM, n=4). FIG. 7D) Liver glycogen levels (mg Glycogen per g liver tissue; means±SEM, n=4). FIG. 7E) Liver triglyceride levels (mg Triglycerides per g liver tissue; means±SEM, n=4). FIG. 7D) Liver glycogen levels (mg Glycogen per g liver tissue; means±SEM, n=4). FIG. 7F) Serum triglyceride levels (mg Triglycerides per ml Serum; means±SEM, n=4). Statistical test FIGS. 7A-7F: Student's t-test.

Figure 8A:
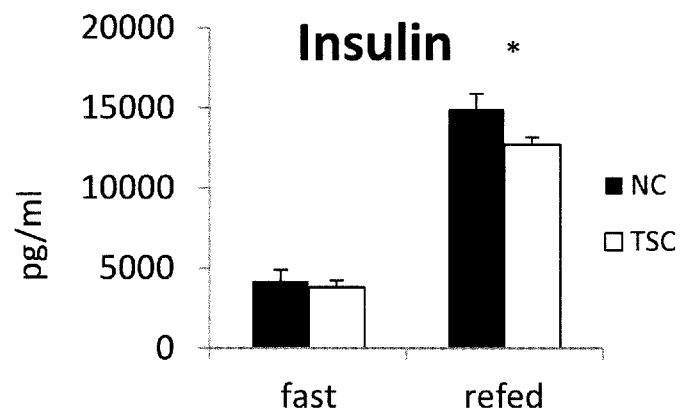
Figure 8B:
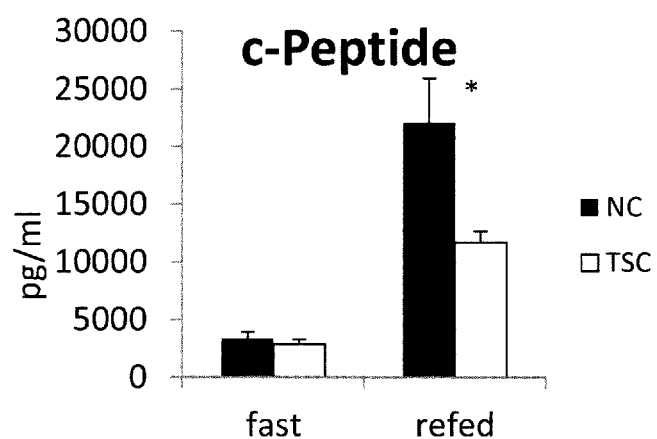
Figure 8C:
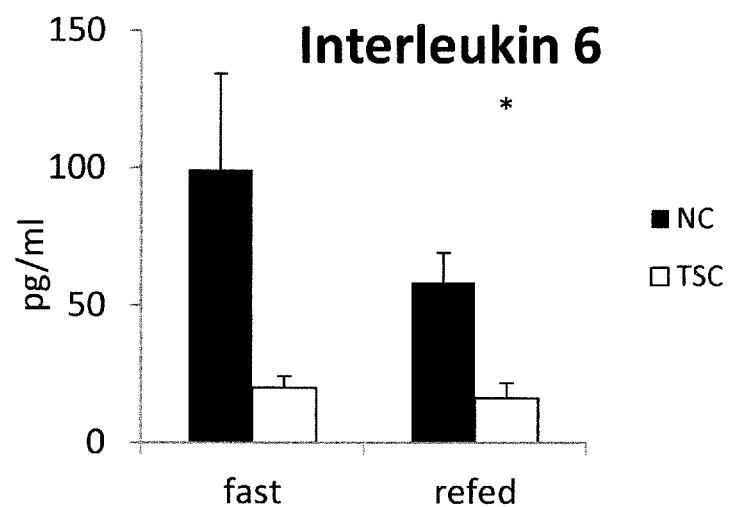
Figure 8D:
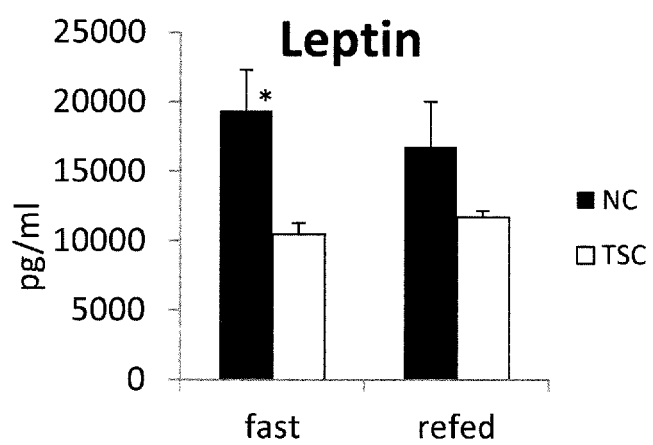
Figure 8E:
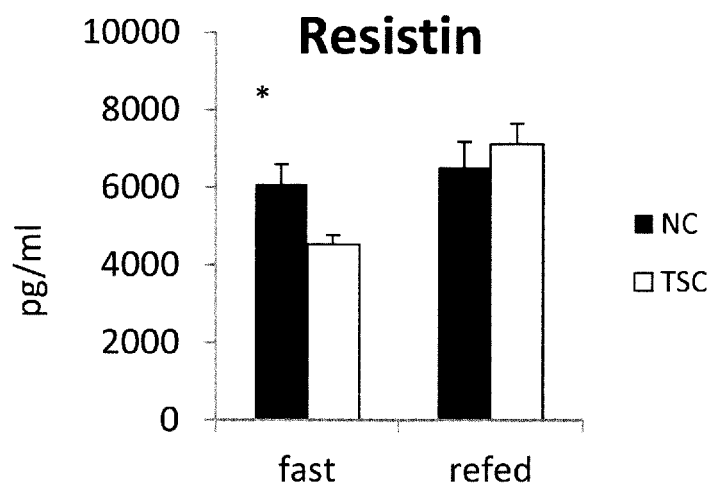
Figure 8F:
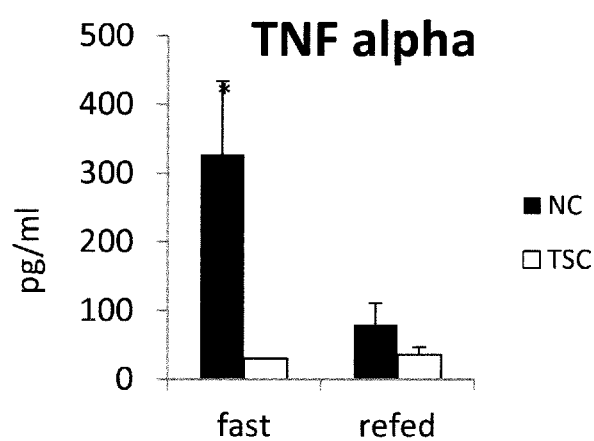
Figure 9A:
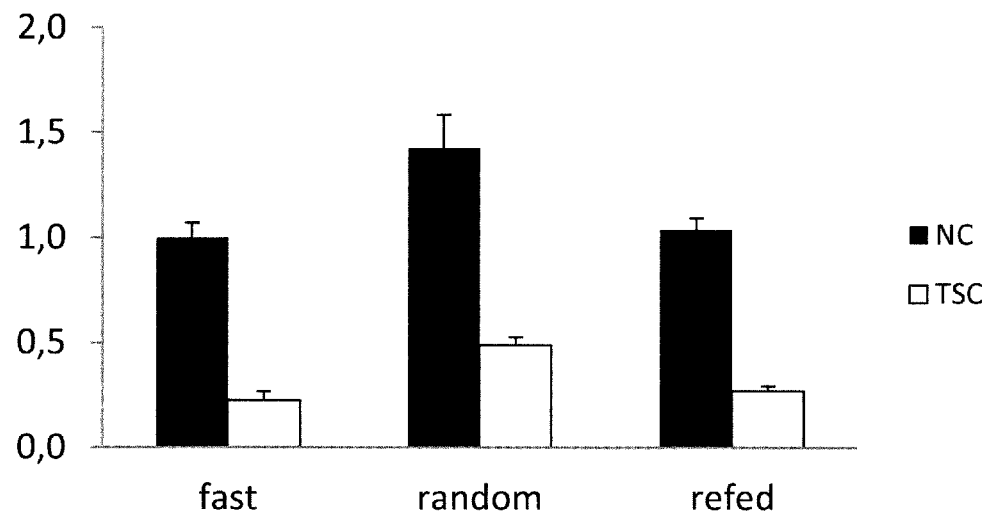
Figure 9B:
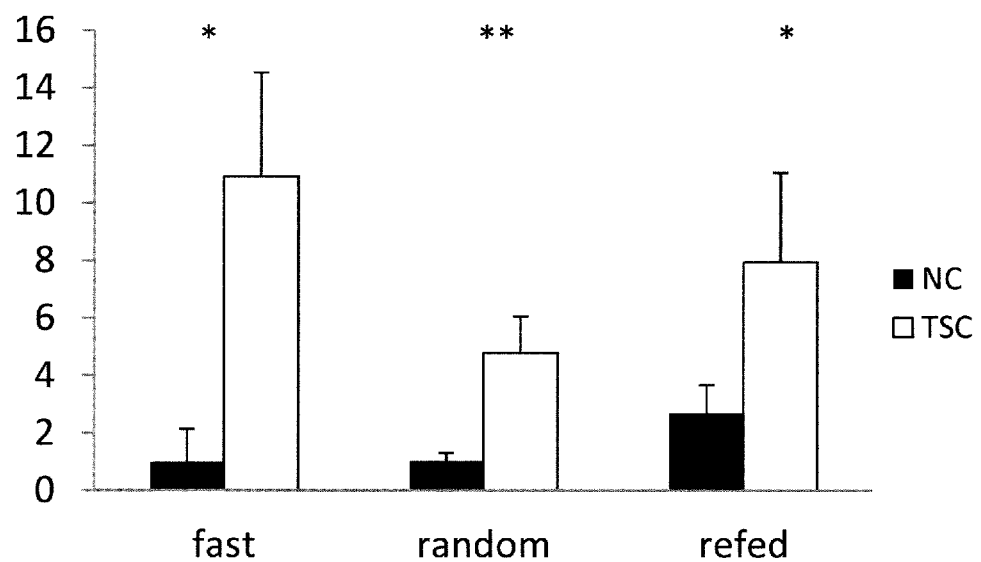
Figure 9C:
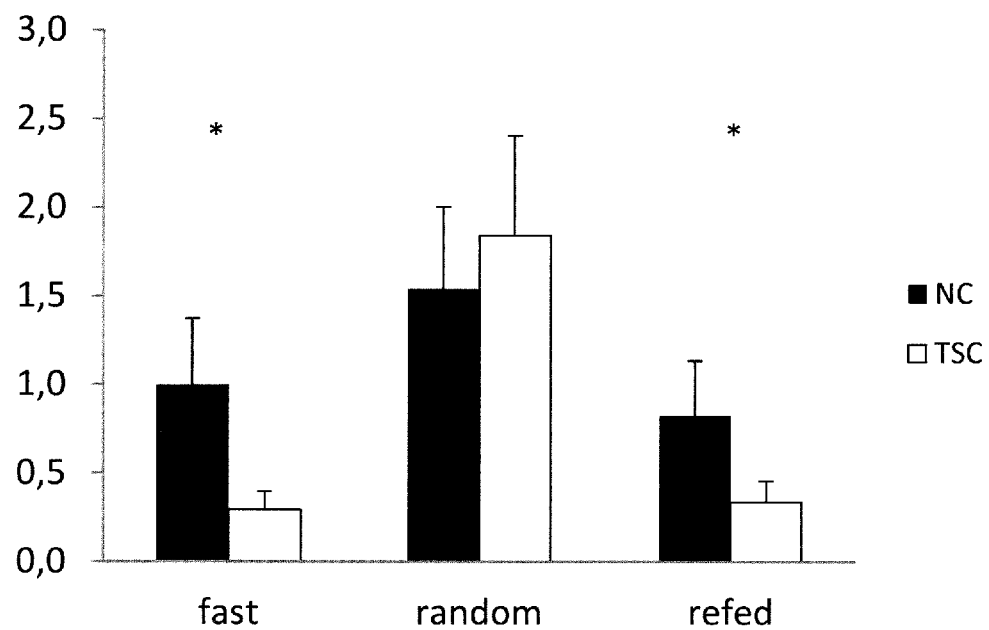
Figure 9D:
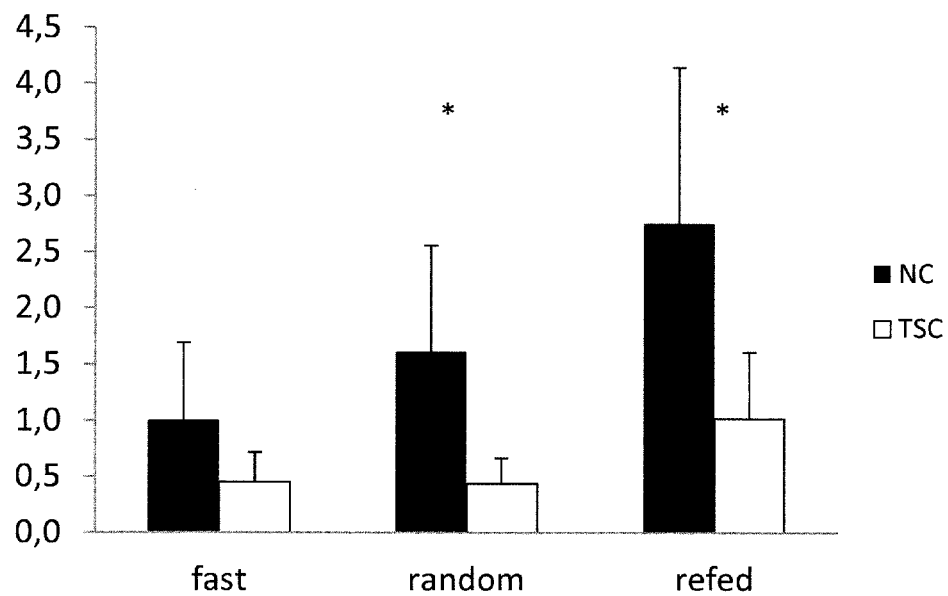

FIGS. 8A-8F show that the hepatic TSC22D4 deficiency improves inflammatory marker expression in diabetic db/db mice. 11 week old db/db mice (same animals as in FIGS. 8A-8F) were injected with control or TSC22D4 shRNA adenovirus. Mice were sacrificed in a fasted (for 18 hours), refed (fasted for 18 hours following 6 hours refeeding), or random fed state. FIG. 8A) Serum Insulin levels in pg/ml (means±SEM, n=4). FIG. 8B) Serum C peptide levels in pg/ml (means±SEM, n=4). FIG. 8C) Serum Interleukin-6 levels in pg/ml (means±SEM, n=4). FIG. 8D) Serum leptin levels in pg/ml (means±SEM, n=4). FIG. 8E) Serum resistin levels in pg/ml (means±SEM, n=4). FIG. 8F) Serum TNF alpha levels in pg/ml (means±SEM, n=4). Statistical test FIGS. 8A-8F: Student's t-test.

FIGS. 9A-9D show that the hepatic knockdown of TSC22D4 in diabetic animals upregulates insulin-sensitizing genes. Quantitative PCR analysis of FIG. 9A) transcription factor transforming growth factor beta 1-stimulated clone 22D4 (TSC22D4), FIG. 9B) Lipocalin 13 (Lcn13), FIG. 9C) Growth factor receptor-bound protein 14 (Grb14), FIG. 9D) suppressor of cytokine signaling 3 (SOCS3), fasted (18 h) and refed state (fasted for 18 h and refed for the following 6 h) (means±SEM, n=7). Statistical test FIGS. 9A-9D: Student's t-test.

Figure 10:
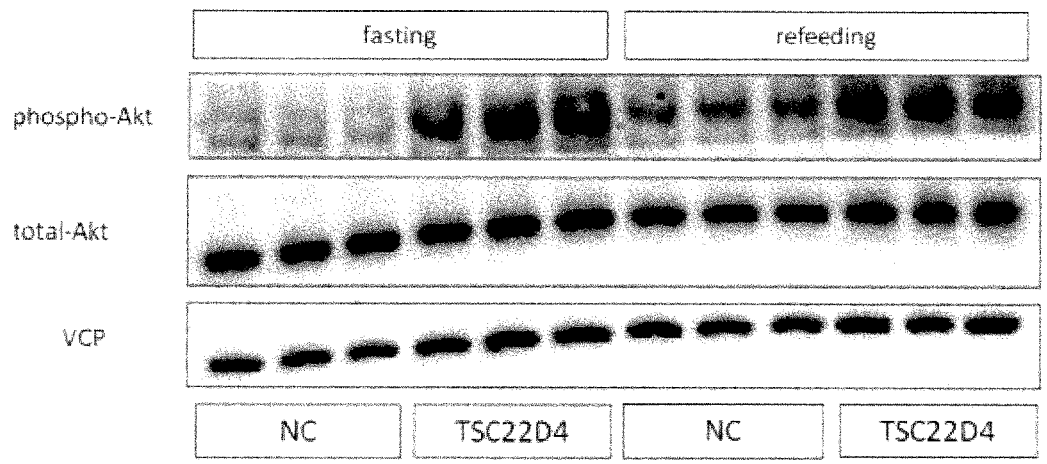

FIG. 10 shows that the loss of TSC22D4 enhances insulin signaling in diabetic livers. Western blot of liver extracts from 11 week old db/db mice (same animals as in FIGS. 8A-8F) injected with control or TSC22D4 shRNA adenovirus. 7 days after injection liver lysates were blotted against total-Aid and Phospho-Akt (Ser473) antibodies (Cell signaling). Mice were sacrificed in a fasted (for 18 hours) or refed (fasted for 18 hours following 6 hours refeeding) state. shRNA-mediated knockdown of TSC22D4 resulted in an increase of Akt-phosphorylation under both fasting and refeeding conditions.

Figure 11:
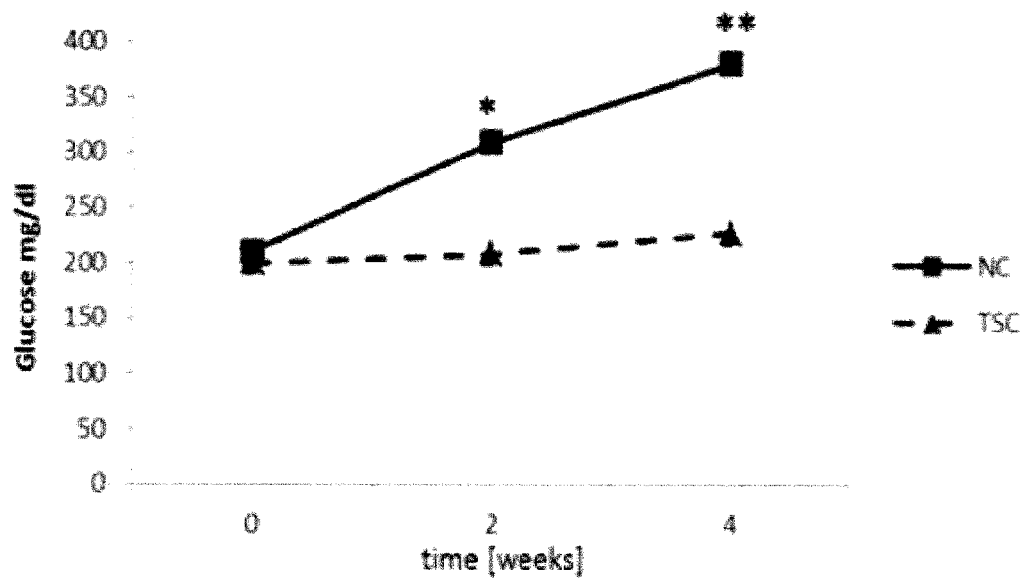

FIG. 11 shows that the hepatocyte-specific inactivation of TSC22D4 prevents hyperglycemia in diabetes-prone mice. db/db mice were injected with an AAV expressing TSC22D4 miRNA at the age of 5 weeks (representing week 0 in the graph) before the onset of overt hyperglycemia. Glucose (mg/dl) was measured at virus injection and at 2 and 4 weeks post virus injection. Prior to glucose measurement mice were fasted for 4 hours. (means±SEM, n=7).

Figure 12A:
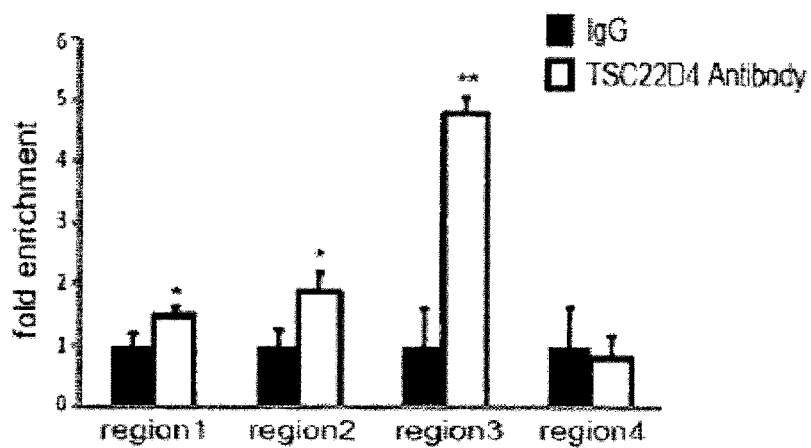
Figure 12B:
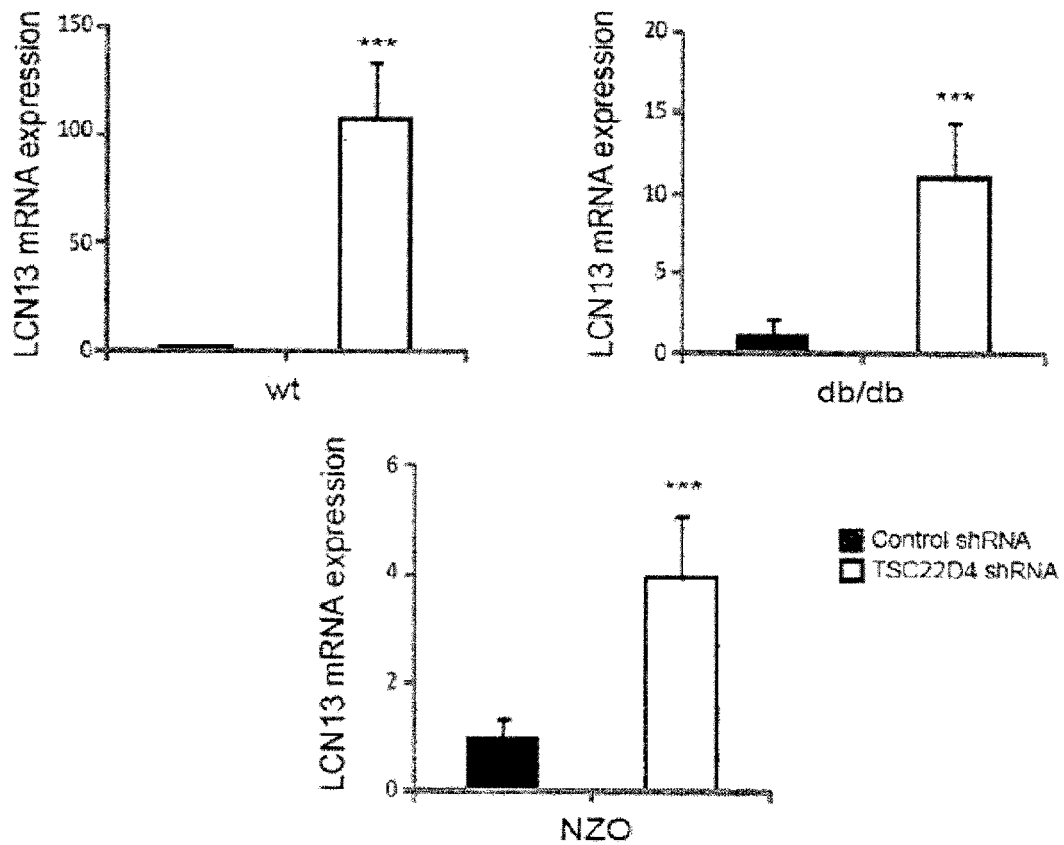
Figure 12C:
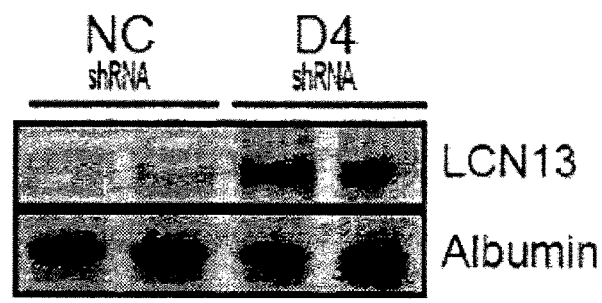
Figure 12D:
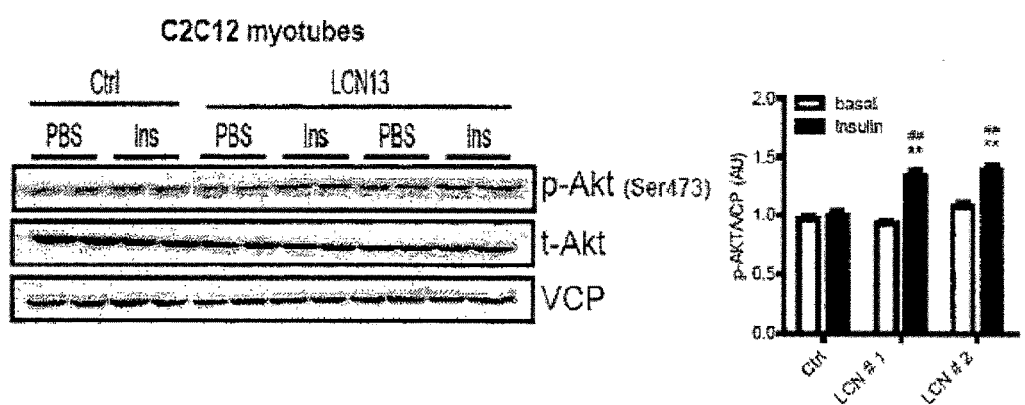
Figure 12E:
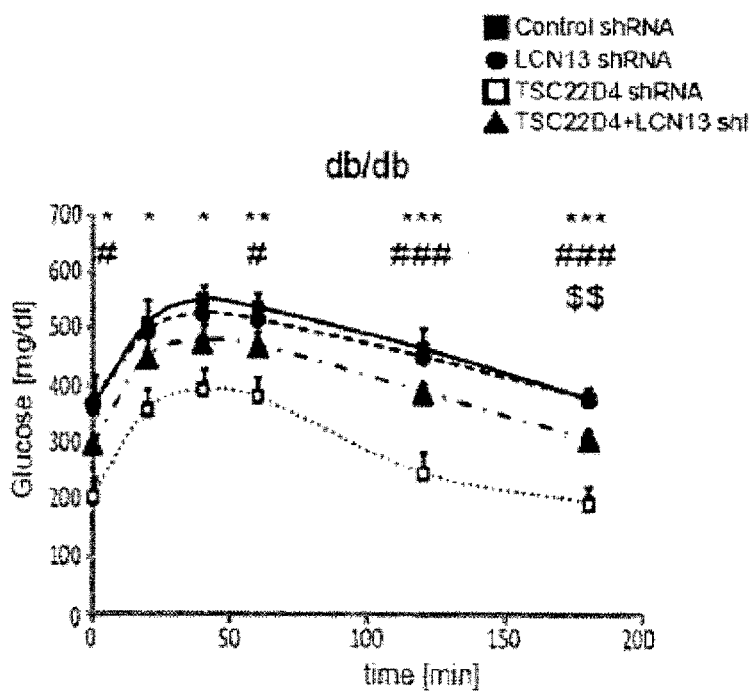
Figure 12F:
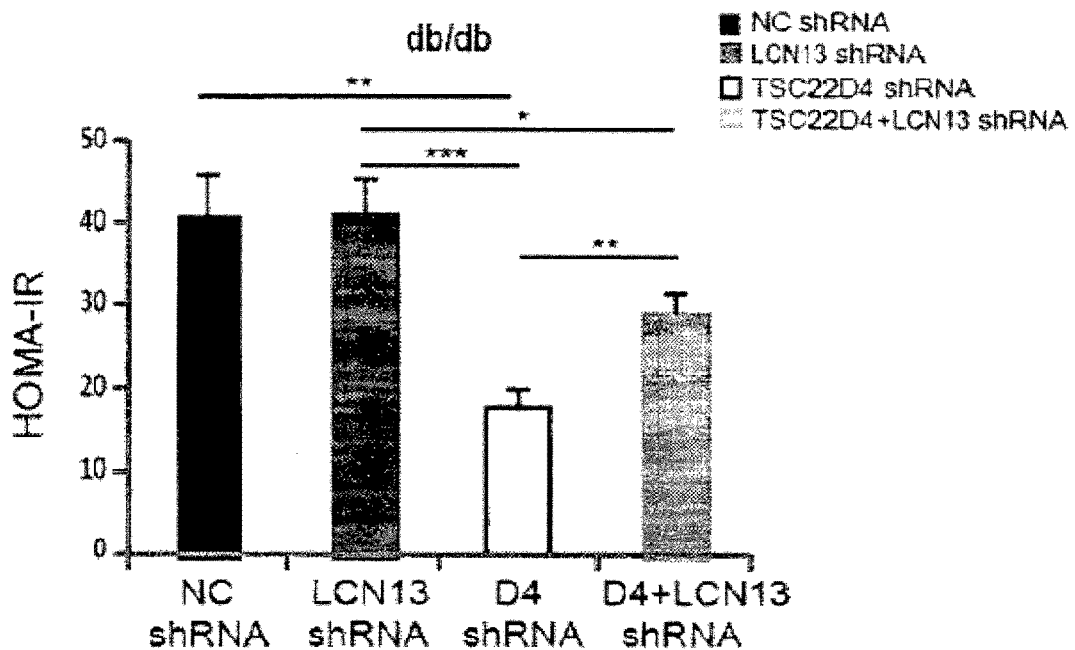
Figure 12G:
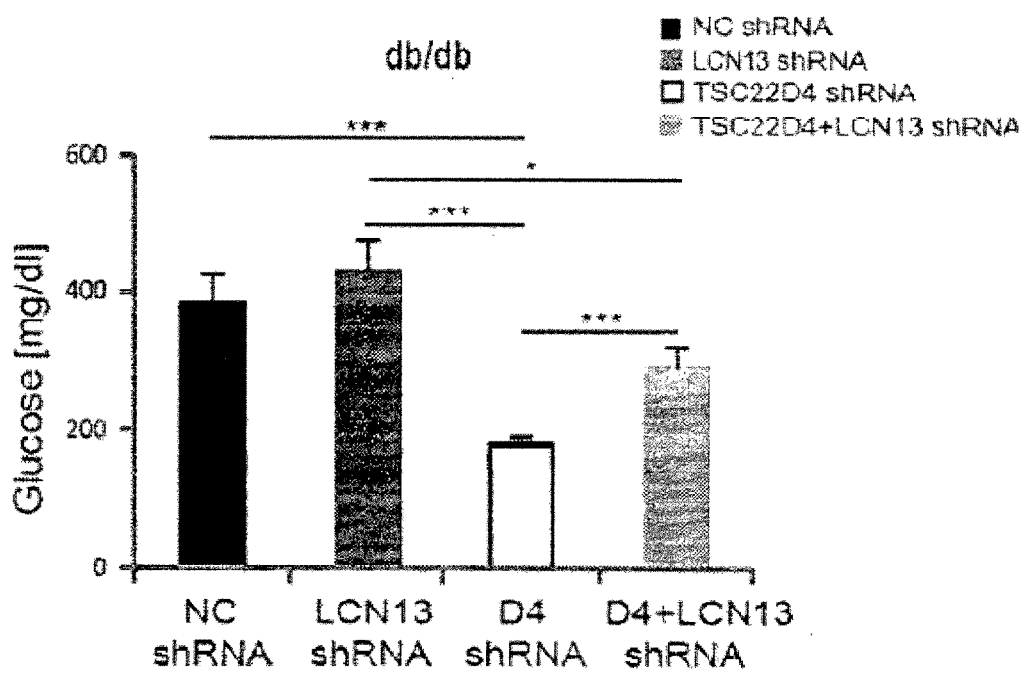
Figure 12H:
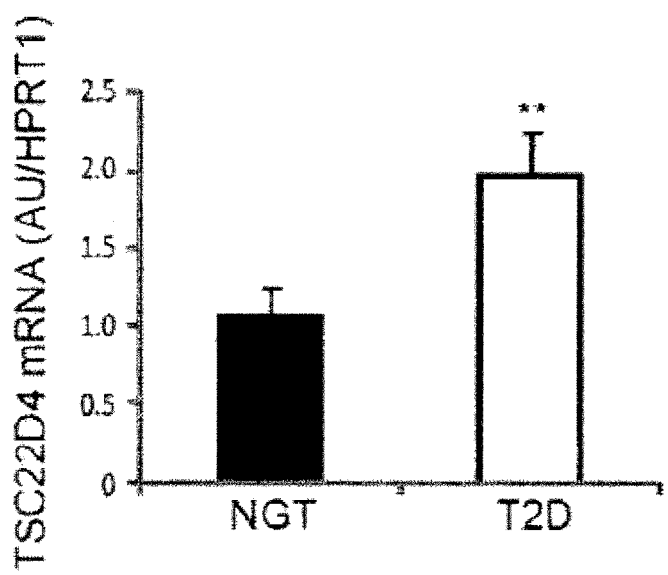
Figure 12I:
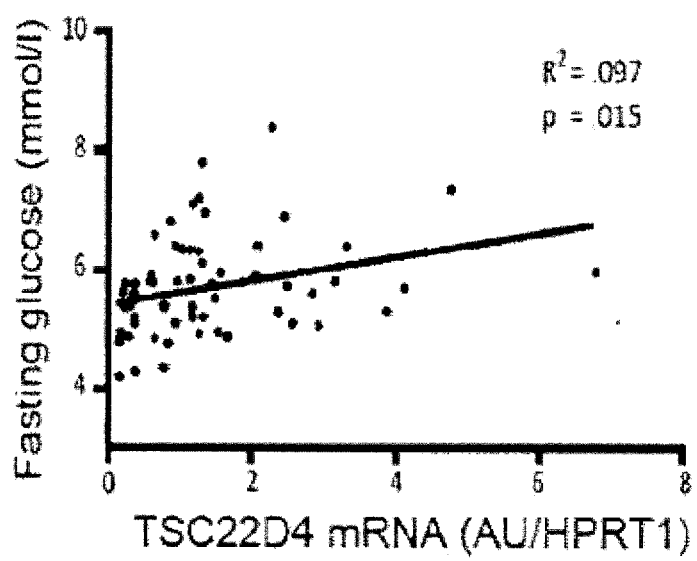

FIGS. 12A-12J show that TSC22D4 acts via the LCN13 endocrine systems and correlates with insulin sensitivity in humans. (FIG. 12A) Chromatin immunoprecipitation of LCN13 promoter regions (1-3) by antibodies against TSC22D4 in livers of wild-type mice. Fold enrichment relative to negative control IgG determined by qPCR. Region 4 represents a negative PCR control (n=2-3). Similar results were obtained by using a different TSC22D4 antibody. (FIG. 12B) Quantitative PCR analysis of LCN13 in livers of control or TSC22D4 shRNA adenovirus-injected wild-type C57Bl/6 (left), db/db (middle) and NZO mice (right) (means±SEM, n≥6 for each experiment). (FIG. 12C) Serum from control (NC shRNA) or TSC22D4 (D4 shRNA) shRNA adenovirus-injected C57Bl/6 mice 7 days after injection was immunoprecipitated with LCN13 antibody and immunoblotted with LCN13 antibody. Albumin antibody was used as loading control. (FIG. 12D) Representative Western blot from control (PBS) or LCN13 (200 nM)-treated C2Cl2 myocyte extracts using total-Akt, phospho-Akt (Ser473), and VCP antibodies. LCN13 (3 h) and insulin treatment for 15 min (30 nM) indicated, respectively. Densitometric analysis shown. **, indicates effect of insulin; ##, indicates effect of LCN13. (FIG. 12E) Glucose tolerance test in control (control shRNA), LCN13 (LCN13 shRNA), TSC22D4 (TSC22D4 shRNA), TSC22D4 plus LCN13 (TSC22D4+LCN13 shRNA) shRNA adenovirus-injected db/db mice 1 week after injection. Glucose was injected i.p. at a concentration of 1 g glucose per kg body weight. * indicates significance between NC and TSC22D4 group; # indicates significance between TSC22D4 and TSC22D4+ LCN13 group; $ indicates significance between NC and TSC22D4+LCN13 group. (FIG. 12F) HOMA IR index in same mice as in FIG. 12E. (FIG. 12G) Serum glucose levels in same mice as in (FIG. 12E). (FIG. 12H) Quantitative PCR analysis of TSC22D4 mRNA expression in livers of patients with type 2 diabetes (T2D, n=26) or normal glucose tolerance (NGT, n=40). (FIG. 12I) Correlation of hepatic expression of TSC22D4 mRNA and fasting plasma glucose in the same patients as in (FIG. 12H). (FIG. 12J) Correlation of human liver expression of TSC22D4 mRNA and glucose infusion rate (GIR) during hyperinsulemic-euglycemic clamp study in the same patients as in (FIG. 12H). Statistical analysis for a, c-f: student's t-test, g-i: Pearson correlation coefficient, *: p≤0.05; : p≤0.01; *: p≤0.001.

FIGS. 13A-13D show (FIG. 13A) the correlation of human liver expression of LCN13 (Obp2a) and TSC22D4 mRNA levels in patients with type 2 diabetes (n=26) or normal glucose tolerance (n=40). (FIG. 13B) Quantitative PCR analysis of LCN13 (Obp2a) mRNA expression in livers of patients with type 2 diabetes (T2D, n=26) or normal glucose tolerance (NGT, n=40). (FIG. 13C) Correlation of human liver expression of LCN13 (Obp2a) mRNA and glucose infusion rate (GIR) during hyperinsulemic-euglycemic clamp study in the same patients as in (a). (FIG. 13D) Correlation of hepatic expression of LCN13 (Obp2a) mRNA and fasting plasma glucose in the same patients as in (a). Statistical analysis for a,c,d: Pearson correlation coefficient, b: student's t-test, *: p≤0.05; : p≤0.01; *: p≤0.001.

Sequence ID NOs. 1 to 4 show oligonucleotides as used in the experiments of the present invention.

EXAMPLES

Recombinant Viruses

Adenoviruses expressing a TSC22D4 or a non-specific shRNA under the control of the U6 promoter, or the TSC22D4 cDNA under the control of the CMV promoter were cloned using the BLOCK-iT Adenoviral RNAi expression system (Invitrogen, Karlsruhe, Germany). Vi-ruses were purified by the cesium chloride method and dialyzed against phosphate-buffered-saline buffer containing 10% glycerol prior to animal injection, as described previously (Herzig S, Hedrick S, Morantte I, Koo S H, Galimi F, Montminy M. CREB controls hepatic lipid metabolism through nuclear hormone receptor PPAR-gamma. Nature. 2003; 426: 190-193. Herzig S, Long F, Jhala U S, Hedrick S, Quinn R, Bauer A, Rudolph D, Yoon C, Puigserver P, Spiegelman B, et al. CREB regulates hepatic gluconeogenesis through the coactivator PGC-1. Nature. 2001; 413: 179-183). AAVs encoding control or TSC22D4-specific miRNAs under the control of a hepatocyte-specific promoter were established as described previously Rose A J, Berriel Diaz M, Reimann A, Klement J, Walcher T, Krones-Herzig A, Stroble O, Werner J, Peters A, Kleyman A, Tuckermann J P, Vegiopoyulos A, Herzig S. Molecular Control of Systemic Bile Acid Homeostasis by the Liver Glucocorticoid Receptor. Cell Metabolism 14: 123-130, 2011).

Animal Experiments

Male 8-12 week old C57Bl/6 and 10 week old db/db mice were obtained from Charles River Laboratories (Brussels, Belgium) and maintained on a 12 h light-dark cycle with regular unrestricted diet. Prior to insulin and glucose tolerance tests, animals were fasted for 4 h. Otherwise, animals were fed ad libitum and had free access to water. For adenovirus injections, $1-2 \times 10^9$ plaque-forming units (pfu) per recombinant virus were administered via tail vein injection. For AAV experiments, $5 \times 10^{11}$ viruses were injected via the tail vein. In each experiment, 6-12 animals received identical treatments and were analyzed under fasted (18 hrs fasting), random fed or fed (18 hrs fasting followed by 6 hrs re-feeding) conditions as indicated. Organs including liver, epididymal and abdominal fat pads, and gastrocnemius muscles were collected after specific time periods, weighed, snap-frozen and used for further analysis. Total body fat content was determined by an Echo MRI body composition analyzer (Echo Medical Systems, Houston, USA). Animal handling and experimentation was done in accordance with NIH guidelines and approved by local authorities.

For the insulin tolerance tests a stock solution of 1 U Insulin/mL was prepared using 0.9% sodium chloride. Mice were fasted for 4 hours prior to the experiment. The body weight of all animals was determined and the blood glucose levels were measured by cutting the tail with a razor blade. The blood drop was put onto a glucometer strip and measured. 1 U insulin/kg body weight was injected to C57Bl/6 and 1.5 U insulin/kg body weight was injected to db/db mice intraperitoneally. The blood glucose levels were monitored after 20, 40, 60, 80 and 120 min.

For the glucose tolerance tests a stock solution of 20% glucose was prepared using 0.9% sodium chloride. Mice were fasted for 4 hours prior to the experiment. The body weight of all animals was determined and the blood glucose levels were measured by cutting the tail with a razor blade. The blood drop was put onto a glucometer strip and measured. 5 μL per gram of 20% glucose solution was injected to C57Bl/6 and db/db mice intraperitoneally. The blood glucose levels were monitored after 20, 40, 60, 80 and 120 min.

Human Subjects

The inventors investigated TSC22D4 mRNA expression in liver tissue samples obtained from 66 extensively characterized Caucasian obese and lean men and women who underwent open abdominal surgery for Roux en Y bypass, sleeve gastrectomy, elective cholecystectomy or explorative laparotomy. With oral glucose tolerance tests, the inventors identified individuals with type 2 diabetes (n=26) or normal glucose tolerance (n=40). Insulin sensitivity was assessed using the euglycemic-hyperinsulinemic clamp method as described. All baseline blood samples were collected between 8 and 10 am after an overnight fast. All study protocols have been approved by the Ethics committee of the University of Leipzig (363-10-13122010 and 017-12-230112). All participants gave written informed consent before taking part in the study.

Blood Metabolites

Serum levels of glucose and triglycerides (TG) were determined using an automatic glucose monitor (One Touch, Lifescan, Neckargemünd, Germany) or commercial kits (Sigma, Munich, Germany; RANDOX, Crumlin, Northern Ireland; WAKO, Neuss, Germany, respectively). Insulin levels were determined using a mouse insulin enzyme-linked immunosorbent assay (Mercodia, Uppsala, Sweden).

Tissue Lipid Extraction

Hepatic lipids were extracted as previously described (Herzig S, Hedrick S, Morantte I, Koo S H, Galimi F, Montminy M. CREB controls hepatic lipid metabolism through nuclear hormone receptor PPAR-gamma. Nature. 2003; 426: 190-193).

Histochemistry

Liver tissue was embedded in Tissue Tek optimal cutting temperature compound (Sakura, Torrance, USA). Five-micrometer cryosections were stained with haematoxylin and eosin or Oil Red O as described (Peet D J, Turley S D, Ma W, Janowski B A, Lobaccaro J M, Hammer R E, Mangelsdorf D J (1998) Cholesterol and bile acid metabolism are impaired in mice lacking the nuclear oxysterol receptor LXR alpha. Cell 93: 693-704).

Quantitative Taqman RT-PCR

Total RNA was extracted from homogenized mouse liver or cell lysates using Qiazol reagent (Qiagen, Hilden, Germany). cDNA was prepared by reverse transcription using the M-MuLV enzyme and Oligo dT primer (Fermentas, St. Leon-Rot, Germany). cDNAs were amplified using assay-on-demand kits and an ABIPRISM 7700 Sequence detector (Applied Biosystems, Darmstadt, Germany). RNA expression data was normalized to levels of TATA-box binding protein (TBP) RNA.

Human TSC22D4 mRNA expression was measured by quantitative real-time RT-PCR in a fluorescent temperature cycler using the TaqMan assay, and fluorescence was detected on an ABI PRISM 7000 sequence detector (Applied Biosystems, Darmstadt, Germany). Total RNA was isolated using TRIzol (Life technologies, Grand Island, N.Y.), and 1 μg RNA was reverse transcribed with standard reagents (Life Technologies, Grand Island, N.Y.). From each RT-PCR, 2 μl were amplified in a 26 μl PCR reaction using the Brilliant SYBR green QPCR Core reagent kit from stratagene (La Jolla, Calif.) according to the manufacturer's instructions. Samples were incubated in the ABI PRISM 7000 sequence detector for an initial denaturation at 95° C. for 10 min, followed by 40 PCR cycles, each cycle consisting of 95° C. for 15 s, 60° C. for 1 min and 72° C. for 1 min. Human TSC22D4 and Obp2a (LCN13) (determined by Hs00229526_m1 and Hs01062934_g1, respectively) (Applied Biosystems, Darmstadt, Germany) mRNA expression was calculated relative to the mRNA expression of hypoxanthine phosphoribosyltransferase 1 (HPRT1), determined by a premixed assay on demand for HPRT1 (Hs01003267_m1) (Applied Biosystems, Darmstadt, Germany). Amplification of specific transcripts was confirmed by melting curve profiles (cooling the sample to 68° C. and heating slowly to 95° C. with measurement of fluorescence) at the end of each PCR. The specificity of the PCR was further verified by subjecting the amplification products to agarose gel electrophoresis.

Protein Analysis

Protein was extracted from frozen organ samples or cultured hepatocytes in cell lysis buffer (Rose A J, Frosig C, Kiens B, Wojtaszewski J F, Richter E A. Effect of endurance exercise training on Ca2+ calmodulin-dependent protein kinase II expression and signaling in skeletal muscle of humans. J Physiol. 2007; 583: 785-795) and 20 μg of protein were loaded onto 4-12% SDS-polyacrylamide gels and blotted onto nitrocellulose membranes. Western blot assays were performed as described (Herzig et al, 2001) using antibodies specific for TSC22D4 (Abcam, Cambridge, UK or Sigma, Munich, Germany), AKT, p-AKT, GSK, p-GSK (Cell signaling, Danvers, USA) or VCP (Abcam).

Plasmids and RNA Interference

For shRNA experiments, oligonucleotides targeting mouse TSC22D4 (GCCTGGTTGGCATTGACAACAC-GAATG; SEQ ID No. 1), were annealed and cloned into the pENTR/U6 shRNA vector (Invitrogen). Non-specific oligonucleotides (5'-GATCTGATCGACACTGTAATG-3' SEQ ID No. 2) with no significant homology to any mammalian gene sequence were used as non-silencing controls in all experiments. For miRNA experiments, oligonucleotides targeting mouse TSC22D4 (5'-GACAGCGATGACGA-TAGTGGT-3' SEQ ID No. 3) and non-specific oligonucleotides (5'-AAATGTACTGCGCGTGGAGAC-3' SEQ ID No. 4) were cloned into the pdsAAV-LP1 vector.

Cell Culture and Transient Transfection Assays

Primary mouse hepatocytes were isolated and cultured as described (Klingmuller U, Bauer A, Bohl S, Nickel P J, Breitkopf K, Dooley S, Zellmer S, Kern C, Merfort I, Sparna T, et al. Primary mouse hepatocytes for systems biology approaches: a standardized in vitro system for modelling of signal transduction pathways. IEE Proc Syst Biol. 2006; 153: 433-447). Briefly, male 8-12 week old C57Bl/6 mice were anaesthetized by i.p. injection of 100 mg/kg body weight ketamine hydrochloride and 5 mg/kg body weight xylazine hydrochloride. After opening the abdominal cavity, the liver was perfused at 37° C. with HANKS I (8 g NaCl, 0.4 g KCl, 3.57 g Hepes, 0.06 g $Na_2HPO_4 \times 2\ H_2O$, 0.06 g $KH_2PO_4$ in 1 L distilled $H_2O$, 2.5 mM EGTA, 0.1% glucose, adjusted to pH 7.4) via the portal vein for 5 min and subsequently with HANKS II (8 g NaCl, 0.4 g KCl, 3.57 g Hepes, 0.06 g $Na_2HPO_4 \times 2\ H_2O$, 0.06 g $KH_2PO_4$ in 1 L distilled $H_2O$, 0.1% glucose, 3 mg/ml collagenase CLSII, 5 mM $CaCl_2$, adjusted to pH 7.4) for 5-7 min until disintegration of the liver structure was observed. The liver capsule was removed and the cell suspension was filtered through a 100 μm mesh. The cells were washed and, subsequently, viability of cells was determined by trypan blue staining. 1000000 living cells/well were seeded on collagen I-coated six-well plates. After 24 h, cells were infected with recombinant adenoviruses at a multiplicity of infection of 100. For stimulation experiments, primary hepatocytes were treated with PBS (control medium) or insulin at a concentration of 100 nM/6-well for 10 minutes. Cells were harvested 48 h after infection.

Cistrome Analysis of Hepatic TSC22D4

KEGG-Pathway analysis of Chip-Sequencing results were sorted by significance. The Insulin signaling pathway was found to be significantly regulated (p=0.00005). Chip-Sequencing was performed in liver extracts from Flag-TSC22D4 cDNA adenovirus-injected male C57Bl/6 mice 7 days after injection.

Figure 12J:
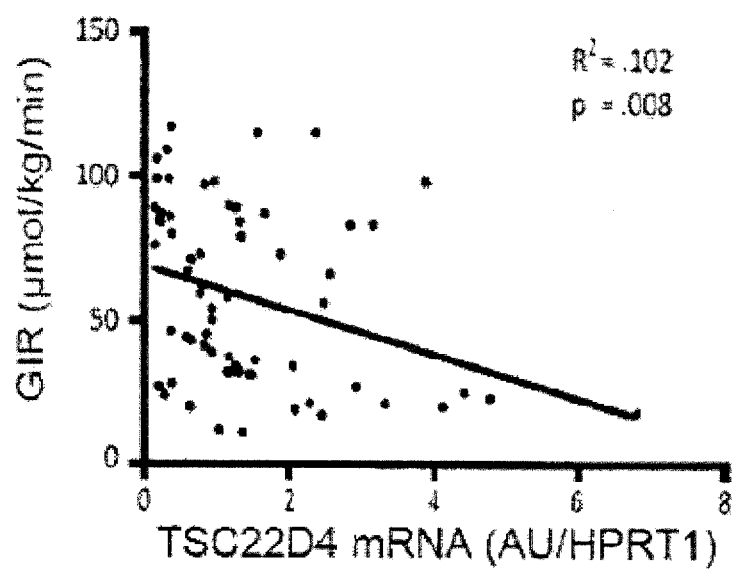
Figure 13A:
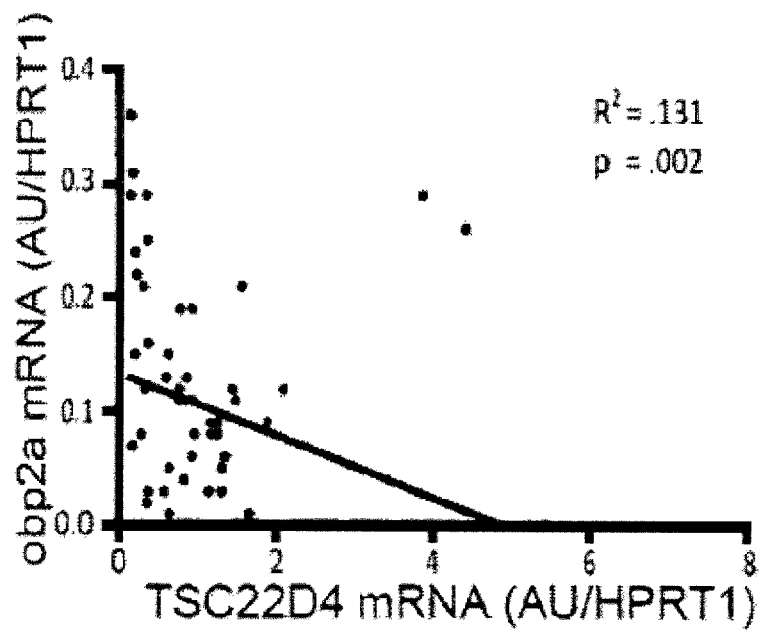
Figure 13B:
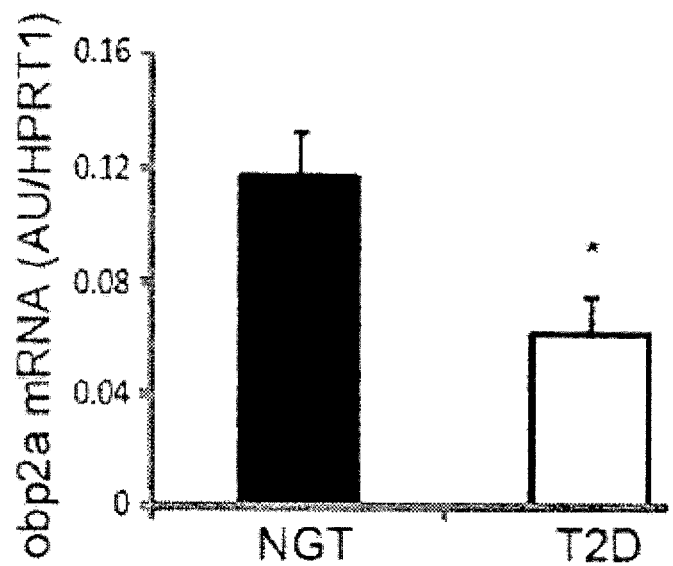
Figure 13C:
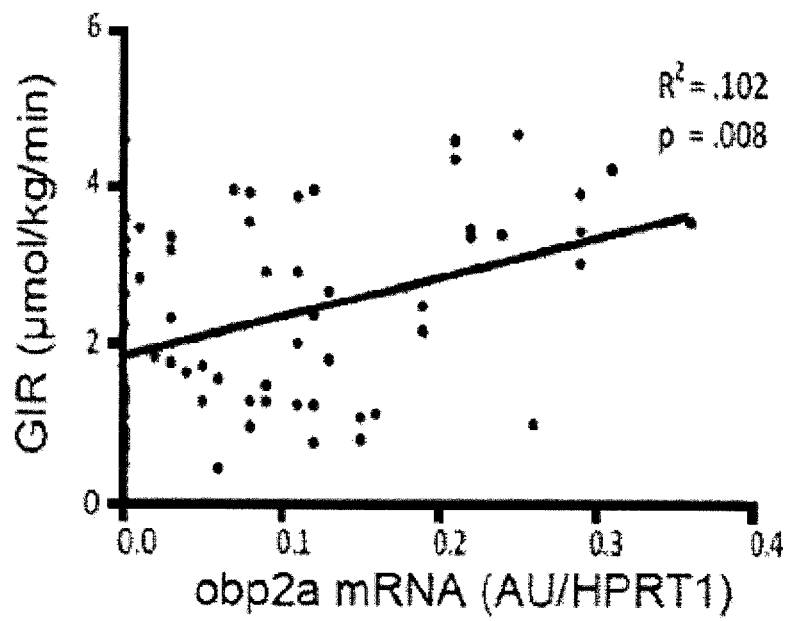
Figure 13D:
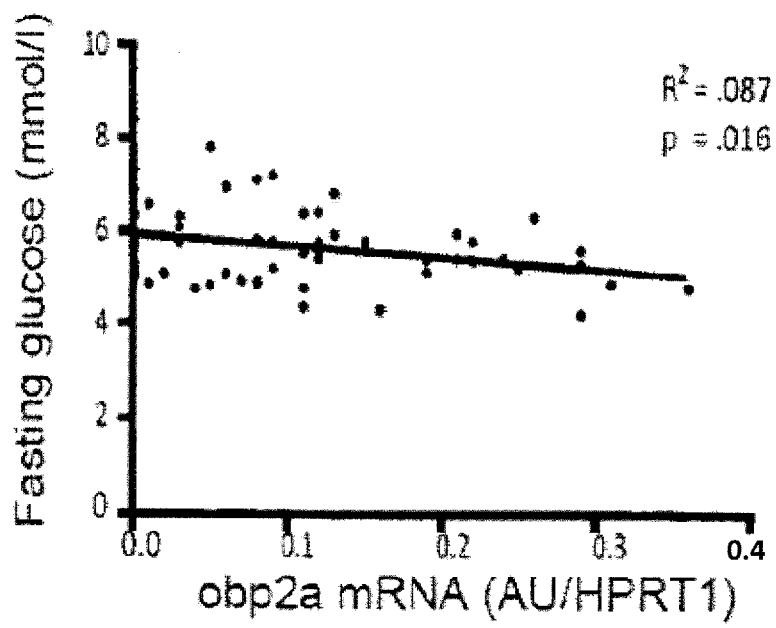

To test the relevance of the findings in the human setting, the inventors analyzed a cohort of 66 patients with normal glucose tolerance (NGT) or type 2 diabetes (T2D). TSC22D4 mRNA was significantly elevated in livers of T2D patients as compared with NGT counterparts (FIG. 12h). Consistent with the insulin-sensitizing and gluco-regulatory functions of TSC22D4 in mice, hepatic TSC22D4 mRNA levels significantly correlated with fasting glucose levels (FIG. 12i) and insulin sensitivity across this human cohort, the latter determined by the glucose infusion rate (GIR) during a hyperinsulinemic-euglycemic clamp (FIG. 12j). TSC22D4 mRNA levels positively correlated with circulating TG and pro-inflammatory cytokine levels, thereby further supporting results from animal models. Importantly, LCN13 expression studies in the patient cohort revealed a highly significant correlation between TSC22D4 and LCN13 mRNA levels, and demonstrated an overall lower expression of LCN13 in diabetic patients as compared with non-diabetic subjects. In addition, hepatic LCN13 mRNA levels correlated with GIR and fasting glucose levels in humans, overall recapitulating the TSC22D4-LCN13-insulin sensitization link in animal models.

Taken together, the data establish TSC22D4 as a critical node in systemic glucose metabolism and insulin sensitivity. Given its upstream regulatory function for the LCN13 endocrine system and the subsequent multi-organ enhancement of insulin sensitivity and glucose storage, it is obvious that TSC22D4 inhibition represents an attractive alternative mode in preventive and curative type 2 diabetes therapy and insulin sensitization.

---

The invention claimed is:

1. A method for treatment of insulin resistance and/or type 2 diabetes and/or for improving insulin sensitivity, wherein said method comprises administering to a subject in need of such treatment and/or improvement, a pharmaceutical composition comprising a modulator that is specific for TSC22D4 function and/or expression and wherein said modulator is an oligonucleotide; and a pharmaceutically acceptable excipient.

2. The method, according to claim 1, wherein said pharmaceutical composition is administered orally, rectally, transmucosally, transdermally, intestinally, parenterally, intramuscularly, intrathecally, direct intraventricularly, intravenously, intraperitoneally, intranasally, intraocularly, or subcutaneously.

* * * * *

UNITED STATES PATENT AND TRADEMARK OFFICE
CERTIFICATE OF CORRECTION

PATENT NO. : 9,879,258 B2  
APPLICATION NO. : 14/787416  
DATED : January 30, 2018  
INVENTOR(S) : Mauricio Berriel Diaz et al.

Page 1 of 1

It is certified that error appears in the above-identified patent and that said Letters Patent is hereby corrected as shown below:

Column 1,  
Line 60, "(alphacell)" should read --(alpha-cell)--.

Column 3,  
Line 12, "dipeptidylpeptidase" should read --dipeptidyl-peptidase--.

Column 4,  
Line 4, "(NM 030935)" should read --(NM_030935)--.

Column 11,  
Line 24, "total-Aid" should read --total-Akt--.

Column 13,  
Line 53, "respectively." should read --respectively).--.

Signed and Sealed this  
Fourteenth Day of August, 2018

Andrei Iancu  
*Director of the United States Patent and Trademark Office*

SEQUENCE LISTING

```
<160> NUMBER OF SEQ ID NOS: 4

<210> SEQ ID NO 1
<211> LENGTH: 27
<212> TYPE: DNA
<213> ORGANISM: mus musculus

<400> SEQUENCE: 1
gcctggttgg cattgacaac acgaatg                                27

<210> SEQ ID NO 2
<211> LENGTH: 21
<212> TYPE: DNA
<213> ORGANISM: artificial sequence
<220> FEATURE:
<223> OTHER INFORMATION: non-specific oligonucleotide

<400> SEQUENCE: 2
gatctgatcg acactgtaat g                                      21

<210> SEQ ID NO 3
<211> LENGTH: 21
<212> TYPE: DNA
<213> ORGANISM: mus musculus

<400> SEQUENCE: 3
gacagcgatg acgatagtgg t                                      21

<210> SEQ ID NO 4
```

```
<211> LENGTH: 21
<212> TYPE: DNA
<213> ORGANISM: artificial sequence
<220> FEATURE:
<223> OTHER INFORMATION: non-specific oligonucleotide

<400> SEQUENCE: 4
aaatgtactg cgcgtggaga c                                              21
```